US008629128B2

(12) United States Patent
Buchta et al.

(10) Patent No.: US 8,629,128 B2
(45) Date of Patent: *Jan. 14, 2014

(54) VITAMIN FORMULATION

(71) Applicant: Stiefel Research Australia Pty Ltd, Rowville (AU)

(72) Inventors: Richard Buchta, Rowville (AU); Robert James Houlden, Rowville (AU); Maria Graziella Larm, Rowville (AU); Leon Loupenok, Rowville (AU); Rose Ye, Rowville (AU)

(73) Assignee: Stiefel West Coast, LLC, Wilmington, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,568

(22) Filed: Sep. 20, 2012

(65) Prior Publication Data

US 2013/0101525 A1    Apr. 25, 2013

Related U.S. Application Data

(63) Continuation of application No. 12/892,572, filed on Sep. 28, 2010, now Pat. No. 8,298,515, which is a continuation of application No. 11/420,700, filed on May 26, 2006, now Pat. No. 8,263,580.

(60) Provisional application No. 60/686,752, filed on Jun. 1, 2005.

(51) Int. Cl.
  *A61K 31/59*   (2006.01)
  *A61K 9/00*    (2006.01)
  *A61K 9/12*    (2006.01)

(52) U.S. Cl.
  USPC ............................ 514/167; 424/400; 424/45

(58) Field of Classification Search
  USPC ............ 424/400, 456, 45; 514/167, 458, 725
  See application file for complete search history.

(56) References Cited

U.S. PATENT DOCUMENTS

| | | |
|---|---|---|
| 3,330,730 A | 7/1967 | Hernandez |
| 3,829,563 A | 8/1974 | Barry et al. |
| 3,896,789 A | 7/1975 | Trancik |
| 3,988,438 A | 10/1976 | Weinstein |
| 4,098,882 A | 7/1978 | Lang et al. |
| 4,185,100 A | 1/1980 | Rovee et al. |
| 4,267,173 A | 5/1981 | Draper |
| 4,293,542 A | 10/1981 | Lang et al. |
| 4,305,936 A | 12/1981 | Klein |
| 4,317,817 A | 3/1982 | Blohm et al. |
| 4,618,344 A | 10/1986 | Wells |
| 4,631,064 A | 12/1986 | Juneja |
| 4,847,068 A | 7/1989 | Dole et al. |
| 4,866,048 A | 9/1989 | Calverley et al. |
| 4,868,192 A | 9/1989 | Totten et al. |
| 4,871,723 A | 10/1989 | Makino et al. |
| 4,935,245 A | 6/1990 | Horn et al. |
| 4,981,677 A | 1/1991 | Thau |
| 4,981,679 A | 1/1991 | Briggs et al. |
| 4,992,478 A | 2/1991 | Geria |
| 5,002,680 A | 3/1991 | Schmidt et al. |
| 5,037,655 A | 8/1991 | Giovanoni |
| 5,063,221 A | 11/1991 | Nishii et al. |
| 5,143,717 A | 9/1992 | Davis |
| 5,167,950 A | 12/1992 | Lins |
| 5,252,331 A | 10/1993 | Curtis et al. |
| 5,292,727 A | 3/1994 | Godtfredsen |
| 5,612,327 A | 3/1997 | Makino et al. |
| 5,643,899 A | 7/1997 | Elias et al. |
| 5,658,559 A | 8/1997 | Smith |
| 5,658,575 A | 8/1997 | Ribier et al. |
| 5,695,778 A | 12/1997 | List |
| 5,721,275 A | 2/1998 | Bazzano |
| 5,733,558 A | 3/1998 | Breton et al. |
| 5,763,426 A | 6/1998 | Hansen et al. |
| 5,772,987 A | 6/1998 | Hansenne et al. |
| 5,789,399 A | 8/1998 | Strube |
| 5,833,960 A | 11/1998 | Gers-Barlag et al. |
| 5,834,511 A | 11/1998 | Schulz et al. |
| 5,886,038 A | 3/1999 | Glenn et al. |

(Continued)

FOREIGN PATENT DOCUMENTS

| | | |
|---|---|---|
| BE | 845.720 A1 | 12/1976 |
| EP | 0 309 353 A2 | 3/1989 |
| EP | 0 421 333 A1 | 4/1991 |
| EP | 0 484 530 A1 | 5/1992 |
| EP | 0 505 108 B1 | 10/1995 |
| EP | 6 676 198 B1 | 10/1998 |
| EP | 0676198 A1 | 10/1998 |
| EP | 0 979 654 A1 | 2/2000 |
| FR | 2 862 540 A1 | 5/2005 |
| RO | 115938 B1 | 3/2000 |
| WO | 85/00519 A1 | 2/1985 |

(Continued)

OTHER PUBLICATIONS

Merriam-Webster Dictionary, www.merriam-webster/dictionary/ointment, 2005.
The Merck Manual, obtained online at http://www.merck.com, Psoriasis and Dermatological Disorders, Cellulitis, SJS and TEN, pp. 1-20, 2009.
Van Der Vleuten, Carine J.M., et al., "In-patient treatment with calcipotriol versus dithranol in refractory psoriasis," European Journal of Dermatology, 1995, pp. 676-679, vol. 5.

(Continued)

*Primary Examiner* — Abigail Fisher
(74) *Attorney, Agent, or Firm* — Nath, Goldberg & Meyer; Joshua B. Goldberg

(57) ABSTRACT

A pharmaceutical aerosol foam composition, comprising: an effective amount of a pharmaceutically active ingredient, wherein said pharmaceutically active ingredient is a vitamin or analogue thereof; an occlusive agent; an aqueous solvent; an organic cosolvent; wherein the pharmaceutically active ingredient is insoluble in both water and the occlusive agent; and the occlusive agent being present in an amount sufficient to form an occlusive layer on the skin, in use. In a second embodiment, an oil-in water emulsion having a vitamin, an occlusive agent; an aqueous solvent; and an organic cosolvent, wherein the occlusive agent is present in an amount sufficient to form an occlusive layer on the skin.

70 Claims, 8 Drawing Sheets

(56) References Cited

U.S. PATENT DOCUMENTS

| | | | |
|---|---|---|---|
| 5,902,805 A | 5/1999 | Breton et al. | |
| 5,976,555 A | 11/1999 | Liu et al. | |
| 5,990,100 A | 11/1999 | Rosenberg et al. | |
| 6,075,056 A | 6/2000 | Quigley, Jr. et al. | |
| 6,114,389 A | 9/2000 | Bouras | |
| 6,126,920 A | 10/2000 | Jones et al. | |
| 6,180,123 B1 | 1/2001 | Mondet | |
| 6,187,763 B1 | 2/2001 | Mochizuki et al. | |
| 6,228,887 B1 | 5/2001 | Kligman et al. | |
| 6,267,957 B1 | 7/2001 | Green et al. | |
| 6,325,990 B1 | 12/2001 | Laurent | |
| 6,423,323 B2 | 7/2002 | Neubourg | |
| 6,524,594 B1 | 2/2003 | Santora et al. | |
| 6,730,288 B1 | 5/2004 | Abram | |
| 6,753,013 B1 | 6/2004 | Didriksen et al. | |
| 6,787,529 B2 | 9/2004 | Hoy et al. | |
| 6,919,076 B1 | 7/2005 | Green et al. | |
| 6,946,120 B2 | 9/2005 | Wai-Chiu So et al. | |
| 6,949,255 B2 | 9/2005 | Baron et al. | |
| 7,029,659 B2 | 4/2006 | Abram | |
| 7,141,237 B2 | 11/2006 | Abram et al. | |
| 7,205,420 B2 | 4/2007 | Shapiro et al. | |
| RE39,706 E | 6/2007 | Hansen et al. | |
| 7,351,869 B2 | 4/2008 | Schwartz et al. | |
| 7,374,747 B2 | 5/2008 | Abram et al. | |
| 7,507,865 B2 | 3/2009 | Vinas et al. | |
| 7,553,835 B1 | 6/2009 | Davey et al. | |
| 7,700,076 B2 | 4/2010 | Tamarkin et al. | |
| 7,820,145 B2 | 10/2010 | Tamarkin et al. | |
| 8,263,580 B2 * | 9/2012 | Buchta et al. | 514/167 |
| 2001/0007866 A1 | 7/2001 | Strube | |
| 2002/0022040 A1 | 2/2002 | Robinson et al. | |
| 2003/0166226 A1 | 9/2003 | Shapiro et al. | |
| 2004/0184992 A1 | 9/2004 | Abram | |
| 2005/0009717 A1 | 1/2005 | Lukenbach et al. | |
| 2005/0031547 A1 | 2/2005 | Tamarkin et al. | |
| 2005/0069566 A1 | 3/2005 | Tamarkin et al. | |
| 2005/0074414 A1 | 4/2005 | Tamarkin et al. | |
| 2005/0075407 A1 | 4/2005 | Tamarkin et al. | |
| 2005/0186142 A1 | 8/2005 | Tamarkin et al. | |
| 2005/0186147 A1 | 8/2005 | Tamarkin et al. | |
| 2005/0205086 A1 | 9/2005 | Tamarkin et al. | |
| 2005/0232869 A1 | 10/2005 | Tamarkin et al. | |
| 2005/0244342 A1 | 11/2005 | Friedman et al. | |
| 2005/0271596 A1 | 12/2005 | Friedman et al. | |
| 2005/0271598 A1 | 12/2005 | Friedman et al. | |
| 2005/0281755 A1 | 12/2005 | Zarif et al. | |
| 2005/0281850 A1 | 12/2005 | Zanutto et al. | |
| 2005/0282788 A1 | 12/2005 | Zanutto et al. | |
| 2006/0018937 A1 | 1/2006 | Friedman et al. | |
| 2006/0029623 A1 | 2/2006 | Astruc et al. | |
| 2006/0034779 A1 | 2/2006 | Arkin et al. | |
| 2006/0057168 A1 | 3/2006 | Larm et al. | |
| 2006/0067894 A1 | 3/2006 | Huggins et al. | |
| 2006/0104912 A1 | 5/2006 | Abram | |
| 2006/0104966 A1 | 5/2006 | Green et al. | |
| 2006/0127321 A1 | 6/2006 | Abram et al. | |
| 2006/0140984 A1 | 6/2006 | Tamarkin et al. | |
| 2006/0193789 A1 | 8/2006 | Tamarkin et al. | |
| 2006/0233721 A1 | 10/2006 | Tamarkin et al. | |
| 2006/0292080 A1 | 12/2006 | Abram et al. | |
| 2007/0020213 A1 | 1/2007 | Tamarkin et al. | |
| 2007/0020304 A1 | 1/2007 | Tamarkin et al. | |
| 2007/0027333 A1 | 2/2007 | Sabroe et al. | |
| 2007/0059253 A1 | 3/2007 | Popp et al. | |
| 2007/0088007 A1 | 4/2007 | Ng et al. | |
| 2007/0196459 A1 | 8/2007 | Zhang et al. | |
| 2007/0215455 A1 | 9/2007 | Folkmann et al. | |
| 2007/0237724 A1 | 10/2007 | Abram et al. | |
| 2007/0253911 A1 | 11/2007 | Tamarkin et al. | |
| 2007/0255066 A1 | 11/2007 | Pedersen et al. | |
| 2007/0292355 A1 | 12/2007 | Tamarkin et al. | |
| 2007/0292359 A1 | 12/2007 | Friedman et al. | |
| 2007/0292461 A1 | 12/2007 | Tamarkin et al. | |
| 2007/0299041 A1 | 12/2007 | Gombart et al. | |
| 2008/0015271 A1 | 1/2008 | Abram et al. | |
| 2008/0031907 A1 | 2/2008 | Tamarkin et al. | |
| 2008/0038374 A1 | 2/2008 | Stahle et al. | |
| 2008/0044444 A1 | 2/2008 | Tamarkin et al. | |
| 2008/0063607 A1 | 3/2008 | Tamarkin et al. | |
| 2008/0069779 A1 | 3/2008 | Tamarkin et al. | |
| 2008/0076742 A1 | 3/2008 | Sheibani et al. | |
| 2008/0102131 A1 | 5/2008 | Nagira et al. | |
| 2008/0138293 A1 | 6/2008 | Tamarkin et al. | |
| 2008/0138296 A1 | 6/2008 | Tamarkin et al. | |
| 2008/0153786 A1 | 6/2008 | Andres et al. | |
| 2008/0161587 A1 | 7/2008 | Schwartz et al. | |
| 2008/0171728 A1 | 7/2008 | Bridges | |
| 2008/0194528 A1 | 8/2008 | Barthez et al. | |
| 2008/0206155 A1 | 8/2008 | Tamarkin et al. | |
| 2008/0206161 A1 | 8/2008 | Tamarkin et al. | |
| 2008/0207570 A1 | 8/2008 | Segura-Orsoni | |
| 2008/0214876 A1 | 9/2008 | Kutner et al. | |
| 2008/0253973 A1 | 10/2008 | Tamarkin et al. | |
| 2008/0281755 A1 | 11/2008 | Brown | |
| 2008/0293681 A1 | 11/2008 | Willcox et al. | |
| 2008/0300229 A1 | 12/2008 | Willcox et al. | |
| 2008/0317679 A1 | 12/2008 | Tamarkin et al. | |
| 2009/0004232 A1 | 1/2009 | Brzokewicz | |
| 2009/0041680 A1 | 2/2009 | Tamarkin et al. | |
| 2009/0130029 A1 | 5/2009 | Tamarkin et al. | |
| 2009/0149473 A1 | 6/2009 | Davey et al. | |
| 2009/0180970 A1 | 7/2009 | Tamarkin et al. | |
| 2010/0040561 A9 | 2/2010 | Tamarkin et al. | |
| 2010/0055137 A1 | 3/2010 | Larm et al. | |
| 2010/0216753 A1 | 8/2010 | Andres et al. | |
| 2010/0266511 A1 | 10/2010 | Abram | |
| 2010/0284938 A1 | 11/2010 | Tamarkin et al. | |

FOREIGN PATENT DOCUMENTS

| | | |
|---|---|---|
| WO | 93/25189 A1 | 12/1993 |
| WO | 96/25194 A1 | 8/1996 |
| WO | 96/27376 A1 | 9/1996 |
| WO | 98/27946 A1 | 7/1998 |
| WO | 99/17739 A1 | 4/1999 |
| WO | 99/36570 A2 | 7/1999 |
| WO | 99/53923 A1 | 10/1999 |
| WO | 00/15193 A1 | 3/2000 |
| WO | 00/64450 A1 | 11/2000 |
| WO | 2004/022034 A1 | 3/2004 |
| WO | 2004/037225 A2 | 5/2004 |
| WO | 2005/018530 A2 | 3/2005 |
| WO | 2006/005844 A1 | 1/2006 |
| WO | 2006/023095 A1 | 3/2006 |
| WO | 2006/024095 A1 | 3/2006 |
| WO | 2006/094064 A2 | 9/2006 |
| WO | 2006/129161 A2 | 12/2006 |
| WO | 2007/012977 A2 | 2/2007 |
| WO | 2007/070643 A2 | 6/2007 |
| WO | 2007/102052 A2 | 9/2007 |
| WO | 2008/012645 A2 | 1/2008 |
| WO | 2008/038140 A2 | 4/2008 |
| WO | 2008/065514 A2 | 6/2008 |
| WO | 2008/110819 A1 | 9/2008 |
| WO | 2008/128782 A2 | 10/2008 |
| WO | 2008/128783 A2 | 10/2008 |
| WO | 2009/008754 A2 | 1/2009 |
| WO | 2009/057136 A2 | 5/2009 |

OTHER PUBLICATIONS

Kragballe, Knud, "Calcipotriol: A New Drug for Topical Psoriasis Treatment," Pharmacology & Tioxicology, 1995, pp. 214-246, vol. 77.

European Pharmacopoeia, 1997, p. 3.

Martindale Extra Pharmacopoeia, 1996, p. xiii.

Nesbitt, Jr., R.U., "Solubility Studies of Silver Sufadiazine," Journal of Pharmaceutical Sciences, 1977, pp. 519-522, vol. 66, No. 4.

"Silver sulfadiazine," Wikipedia, [Online] Dec. 8, 2006, pp. 1-2, Retrieved from the Internet on Jan. 25, 2007: http://en.wikipedia.org/wiki/Silver_sulfadiazine.

Walker, Morton, H., "A Hydrocortisone-Pantothenylol Aerosol Foam for Skin Therapy," Journal of the American Podiatry Association, 1962, pp. 198-202, vol. 52, No. 3.

(56) References Cited

OTHER PUBLICATIONS

Woodford, R., et al., "Bioavailablity and Activity of Topical Corticosteroids from a Novel Drug Delivery System, the Aerosol Quick-Break Foam," Journal of Pharmaceutical Sciences, 1977, pp. 99-103, vol. 66, No. 1.

Wepierre, J., et al., "Factors in the occlusivity of aqueous emulsions," J. Soc. Cosmet. Chem., 1982, pp. 157-167, vol. 33.

Ricciatti-Sibbald, Debra, et al., "Dermatologic Vehicles," Clinics in Dermatology, 1989, pp. 11-24, vol. 7, No. 3.

"Cutivate" Cream product, Physicians' Desk Reference, 1996, pp. 1088-1089, 50th edition.

"Diprolene" AF Cream product, Physicians' Desk Reference, 1996, pp. 2352-2354, 50th edition.

"Epifoam" Aerosol Foam product, Physicians' Desk Reference, 1996, pp. 2399-2400, 50th edition.

"Temovate" Cream product, Physicians' Desk Reference, 1996, pp. 1179-1181, 50th edition.

"Temovate" Emollient Cream product, Physicians' Desk Reference, 1996, pp. 1179-1181, 50th edition.

"Temovate" Ointment product, Physicians' Desk Reference, 1996, pp. 1179-1181, 50th edition.

"Temovate" E Emollient Cream product, Physician's Desk Reference, 1996, pp. 1179-1181, 50th edition.

Physicians' Desk Reference, 1996, 50th Edition, Medical Economies Co.

Physicians' Desk Reference, 1997, 51st Edition, Medical Economies Co.

U.S. Appl. No. 12/318,339, "Foam Composition Kits," filed Dec. 24, 2008, (not published).

Ansel, H.C., Ph.D., et al., "Pharmaceutical Dosage Forms and Drug Delivery Systems", 1990, Lea & Febiger, 5th Edition, seven (7) pages: including book cove pages, preface and table of contents.

Ansel, H.C., Ph.D., et al., "Pharmaceutical Dosage Forms and Drug Delivery Systems", 1990, Chapter 9, pp. 307-346, Lea & Febiger, 5th Edition.

Ansel, H.C., Ph.D., et al., "Pharmaceutical Dosage Forms and Drug Delivery Systems", 1990, Chapter 12, pp. 390-405, Lea & Febiger, 5th Edition.

Extended European Search Report issued Sep. 15, 2010, in counterpart European Application No. 06755917.9.

Houseman, Tamara Salam, et al., "Patients with Psoriasis Prefer Solution and Foam Vehicles: A Quantitative Assessment of Vehicle Preference," Cutis, 2002, pp. 327-332, vol. 70, No. 6.

Bessho, S., et al., "Orally admiistrable stable prepn. of hydroxy-vitamin=D cpds.—by adding stabilisers e.g. tocopherol cpds. to oily hydroxy-vitamin=D cpd. solns.," 1978, WPI / Thomson, XP-002441918.

Surber, et al., Pharmaceutical Research, 1993, 10(9), 1291-1294.

Search Report, Notice of Reasons of Rejection, P2008-514216, dated Mar. 6, 2012, four (4) pages.

Ansel, H.C. et al., Ch. 13 "Aerosols, Inhalations, and Sprays" in "Pharmaceutical Dosage Forms and Drug Delivery Systems," 1995, 6th edition, p. 443-459.

\* cited by examiner

A

B

VITAMIN FORMULATION

CROSS-REFERENCES TO RELATED APPLICATIONS

This application is a Continuation Application of U.S. patent application Ser. No. 12/892,572 filed on Sep. 28, 2010, which is a Continuation of U.S. patent application Ser. No. 11/420,700, filed on May 26, 2006, which claims benefit from U.S. Provisional Patent Application No. 60/686,752 under 35 U.S.C. 119(e) filed on Jun. 1, 2005, the content of each of which is hereby incorporated by reference in its entirety.

BACKGROUND OF THE INVENTION

The present invention provides a composition for the topical administration of pharmaceutical active ingredients.

Various aerosol and non-aerosol quick breaking and slow breaking foams for the topical delivery of pharmaceutical active ingredients are known in the prior art. For example, the foam composition can be an aqueous emulsion system, which upon actuation, produces a stabilized, homogeneous, expandable foam which breaks easily with shear. A composition of this type is often referred to as an aerosol foam or "mousse". Alternatively, the foam composition can be a slow-breaking foam, which collapses only upon more vigorous rubbing.

It is known to use mousse compositions to topically deliver pharmaceutical active ingredients. An example of such a composition is in Australian patent application 80257/87 which discloses a mousse composition for the topical delivery of the pharmaceutically active ingredient, minoxidil. However the efficiency of such systems to deliver pharmaceutically active ingredients is limited.

Moreover, the majority of topical lotions and creams known or suggested in the prior art for delivering pharmaceutically active ingredients contain large amounts of petrolatum or some other occlusive agent to act as a barrier over the skin. This barrier reduces the evaporation of moisture from the skin which leads to increased moisture in the stratum corneum and in the epidermis and enhances the topical delivery of the pharmaceutical active ingredients.

However, in practice it would not be desirable to include such large amounts of an occlusive agent in a mousse formulation because when dispensed the mousse formulation would be a less stable foam, and upon application, the occlusive agent would leave a greasy, sticky lather on the skin which would not be considered acceptable to the consumer.

In U.S. Pat. Nos. 5,002,680 and 4,981,677, there is disclosed mousse compositions that contain an occlusive agent such as petrolatum. These compositions are directed towards cosmetic purposes, and provide no disclosure on their suitability or otherwise to enhance the topical delivery of pharmaceutical active ingredients. Further, in respect of U.S. Pat. No. 4,981,677 the formulation includes a starch component. It is accordingly not apparent that an occlusive layer would be formed.

Accordingly, it would be a significant advance in the art if a mousse composition could be provided that enhanced the topical delivery of the pharmaceutical active ingredient while preferably still providing a pharmaceutically elegant and consumer acceptable composition.

BRIEF SUMMARY OF THE INVENTION

The present invention provides a mousse composition having enhanced topical delivery of a pharmaceutical active ingredient while preferably still providing a pharmaceutically elegant and consumer acceptable composition. As such, in one embodiment, the present invention provides a pharmaceutical aerosol foam composition, comprising: an effective amount of a pharmaceutically active ingredient, wherein the pharmaceutically active ingredient is a vitamin or analogue thereof;
an occlusive agent;
an aqueous solvent;
an organic cosolvent; wherein the pharmaceutically active ingredient is insoluble in both water and the occlusive agent; and the occlusive agent being present in an amount sufficient to form an occlusive layer on the skin, in use.

In certain aspects, the pharmaceutical aerosol foam composition further comprises a stabilizer, such as a vitamin E or a derivative thereof. Preferably, the pharmaceutically active ingredient comprises a vitamin or analogue such as for example, calcipotriene, tretinoin, or acitretin.

In certain preferred aspects, the pharmaceutical aerosol foam composition further comprising an emulsifier. The occlusive agent is preferably petrolatum. The aerosol foam may have a propellant blend of approximately 55% propane, 30% n-butane, and 15% isobutane.

In yet another embodiment, the present invention provides a topical oil-in-water emulsion, the emulsion having a water phase and an oil phase, comprising:
a vitamin or analogue thereof, wherein the vitamin or analogue thereof is solubilized in the water phase and a stabilizer is solubilized in the oil phase;
an emulsifier;
an occlusive agent; and an organic co-solvent.

In a preferred aspect, the emulsion is an aerosol emulsion, which is a foam when released from a pressurized container. The vitamin or analogue thereof is typically vitamin A, vitamin D, or analogues thereof. In a preferred aspect, the vitamin D or analogue thereof is calcipotriene. Other vitamin analogues include for example, vitamin A or analogue thereof, such as tretinoin or acitretin.

In certain aspects, the vitamin or analogue thereof is first solubilized in propylene glycol. Vitamin E or a derivative thereof is the preferred stabilizer. The vitamin or analogue may be a combination of calcipotriene and tretinoin.

In yet other aspects, the vitamin or analogue is present in an amount of from approximately 0.0001% by weight to approximately 10% by weight, based on the total weight of the composition. Moreover, in still other aspects, the emulsion comprises water in an amount up to 90% w/w, based on the total weight of the composition. Preferably, the emulsion comprises water in an amount of from about 40% to about 60% w/w, based on the total weight of the composition.

In still other aspects, the emulsifier is for example, a non-ionic, cationic or anionic surfactant, a fatty alcohol, a fatty acid or fatty acid salts thereof. In one aspect, the emulsifier is a mixture of a $C_{14}$-$C_{22}$ alcohol and a polyoxyethylene fatty alcohol ether. In another aspect, the $C_{14}$-$C_{22}$ alcohol is selected from cetyl alcohol, stearyl alcohol, and a mixture thereof. Preferably, the $C_{14}$-$C_{22}$ alcohol is a mixture of cetyl alcohol and stearyl alcohol. The emulsifier can be in an amount of from approximately 1 to 15% by weight, based on the total weight of the composition. For example, the amount of the $C_{14}$-$C_{22}$ alcohol present is from about 0.5% to about 5% w/w, based on the total weight of the composition.

In certain other aspects, the occlusive agent of the composition is selected from a mineral oil, grease, petrolatum, a fatty acid, an animal fat, a vegetable fat, a water insoluble polymer or a mixture thereof. In one aspect, the occlusive agent is present in an amount of about 1% to about 55% by weight based on the total weight of the composition. In another aspect, the occlusive agent is present in an amount of approximately 1% to about 10% by weight, based on the total weight of the composition. In yet another aspect, the occlusive agent is present in an amount of approximately 5% to about 55% by weight, based on the total weight of the composition. The topical oil-in-water emulsion may further comprise a buffering agent, to obtain for example, a pH of the composition from about pH 4.0 to about pH 9.0. The topical oil-in-water emulsion can also comprise a viscosity reducer.

In certain other aspects, the emulsion further comprises a humectant. In other embodiments, the emulsion further comprises an aerosol propellant selected from a hydrocarbon, a chlorofluorocarbon, dimethyl ether, hydrofluorocarbons and a mixture thereof. Preferably, the aerosol propellant comprises a mixture of hydrocarbons. The emulsion can be a cream, an ointment, a gel, a post-foaming gel, a paste, or a lotion.

In yet another embodiment, the present invention provides a method for treating a dermatological disorder in a mammal, the method comprising: administering a topical oil-in-water emulsion of any of the compositions as herein described to treat the dermatological disorder. The dermatological disorder can be psoriasis.

In yet another embodiment, the present invention provides a method for stabilizing a vitamin or an analogue thereof in a topical oil-in-water emulsion having a water phase and an oil phase, the method comprising: providing a vitamin or an analogue thereof, wherein the vitamin or analogue thereof is solubilized in the water phase; and providing a stabilizer solubilized in the oil phase, wherein the vitamin or analogue thereof is stabilized in the water phase by the presence of the stabilizer solubilized in the oil phase. The vitamin or analogue thereof solubilized in water is preferably first solubilized in propylene glycol.

In still yet another embodiment, the present invention provides a use of a topical oil-in-water emulsion as herein described in the manufacture of a medicament for the treatment of a dermatological disorder.

These and other aspects, objects and embodiments will become more apparent when read with the following figures and detailed description.

DETAILED DESCRIPTION OF THE INVENTION

Figure 1:
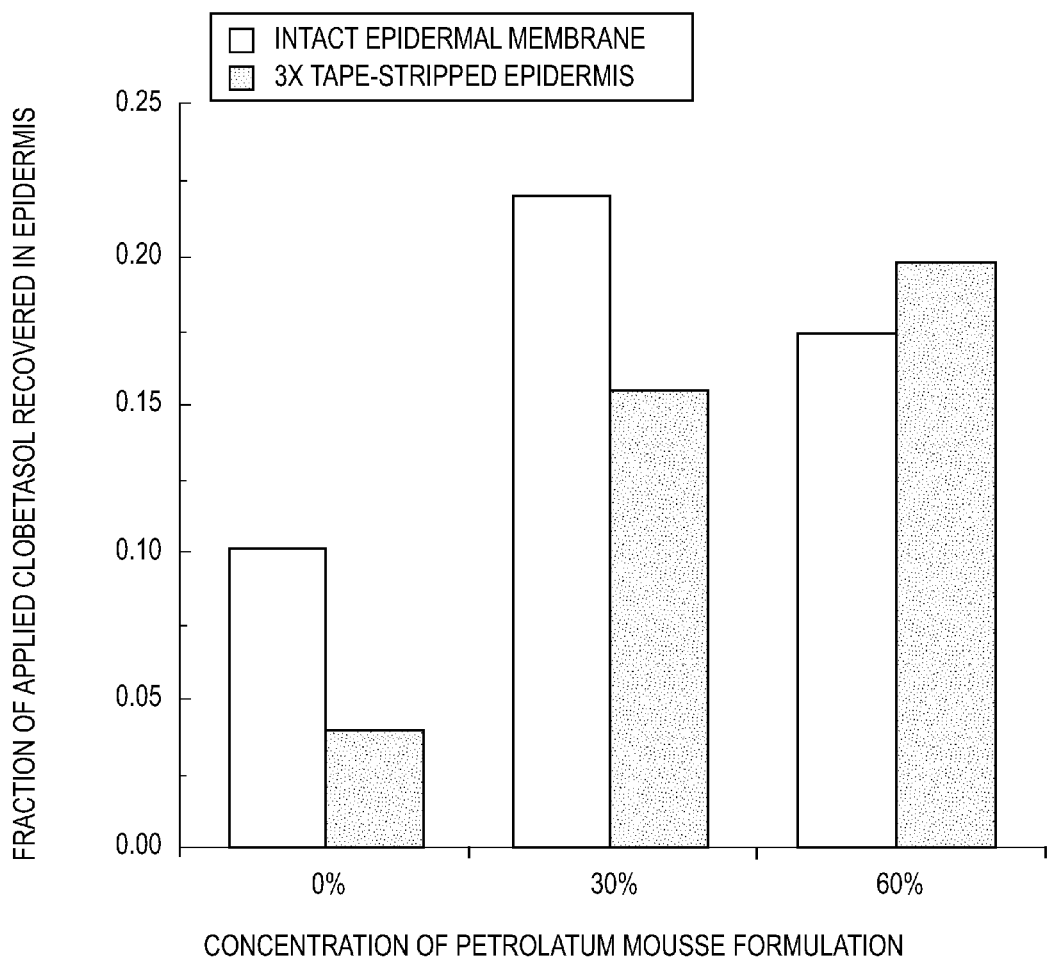
FIG. 1 illustrates the effect of petrolatum content on in vitro epidermal penetration of clobetasol from topical mousse formulations 72 hours after application of 10 mg/cm$^2$ of formulation.
Figure 2:
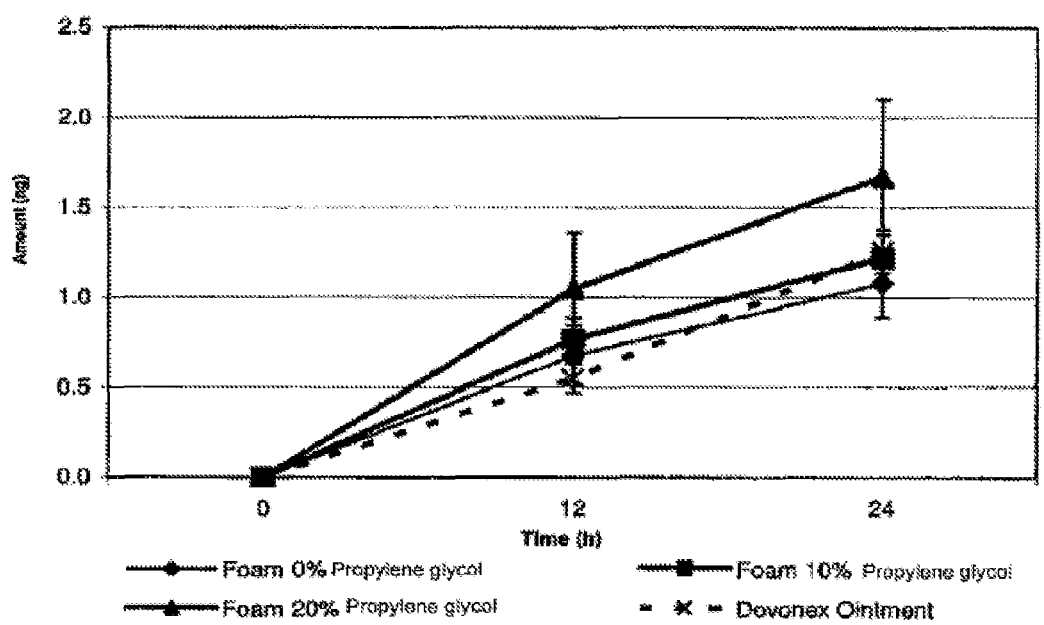
FIG. 2 illustrates the cumulative amount of calcipotriene penetration through fresh dermatomed human skin membrane (250 μm) following application of a calcipotriene aerosol foam composition with varying amounts of propylene glycol (0%; 10%; 20% versus ointment).
Figure 3:
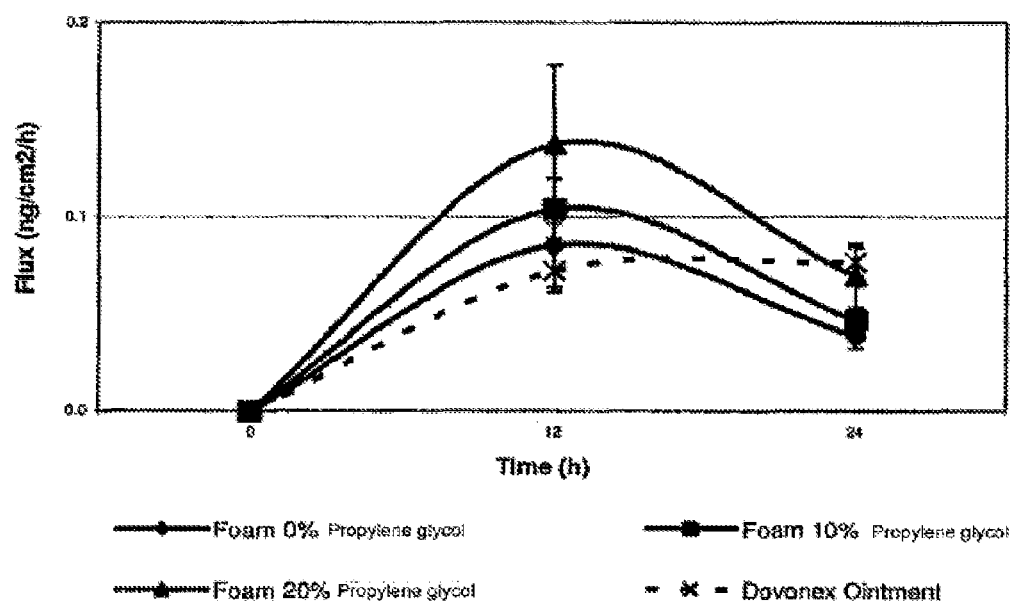
FIG. 3 illustrates the flux profile of calcipotriene following application of an aerosol foam composition with varying amounts of propylene glycol (0%; 10%; 20% versus ointment).
Figure 4:
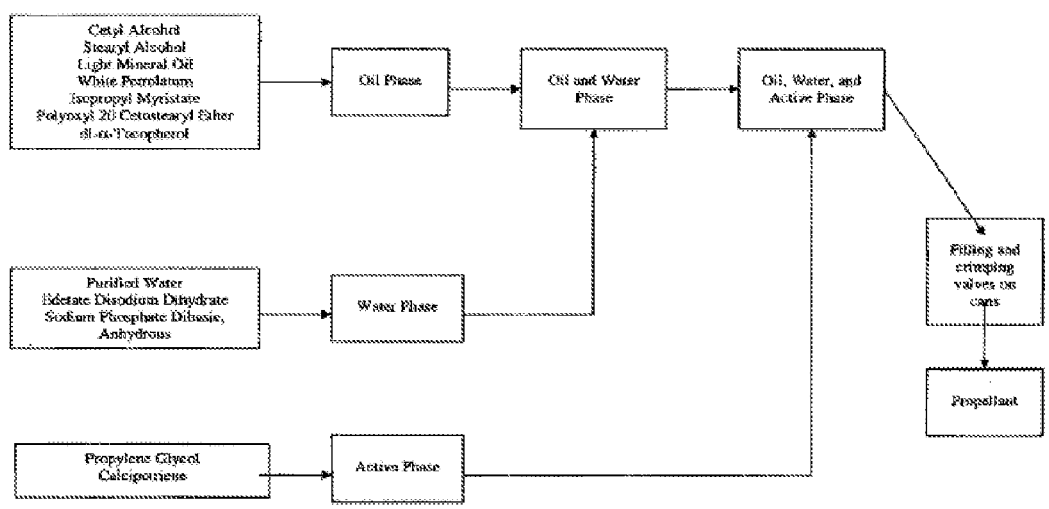
FIG. 4 illustrates a manufacturing flow diagram of one embodiment of the present invention.

I. Pharmaceutical Compositions and Methods of Treating

The present invention is predicated in-part, on the surprising discovery that a mousse formulation with a relatively low amount of an occlusive agent is still able to reduce transepidermal water loss and hence in theory increase skin permeability to effect greater drug skin penetration while remaining an elegant and consumer acceptable composition.

The water-insoluble pharmaceutically active ingredient may be any suitable type. An analgesic such as capsaicin or piroxicam, antifungal such as clotrimazole or miconazole nitrate, antibacterial such as nitrofurazone or gramcidin, anaesthetic such as benzocaine or lidocaine, antiviral such as aciclovir or penciclovir, antipruritic such as crotamiton or phenol, antihistamine such as chlorpheniramine or triprolidine, xanthine such as caffeine, sex hormone such as oestradiol or testosterone, anti-inflammatory agent or corticosteroid may be used. The corticosteroids may be selected from one or more of the group consisting of, betamethasone valerate and clobetasol propionate. A preferred pharmaceutical active agent is a vitamin, such as vitamin A, vitamin D (e.g., $D_3$) and analogues thereof.

In addition to the corticosteroids discussed above, the compositions of the present invention can further include a corticosteroid such as those set forth in U.S. Pat. No. 6,126,920, which is incorporated herein by reference. Suitable corticosteroids include for example, alclometasone dipropionate, fluclorolone acetonide, amcinonide, fluocinolone acetonide, beclamethasone dipropionate, fluocinonide, betamethasone benzoate, fluocortin butyl, betamethasone dipropionate, fluocortolone preparations, betamethasone valerate, fluprednidene acetate, budesonide, flurandrenolone, clobetasol propionate, halcinonide, clobetasone butyrate, hydrocortisone, desonide, hydrocortisone acetate, desoxymethasone, hydrocortisone butyrate, diflorasone diacetate, methylprednisolone acetate, diflucortolone valerate, mometasone furoate, flumethasone pivalate, triamcinolone acetonide, and pharmacologically effective mixtures thereof.

Combinations of active ingredients are also within the scope of the present invention.

Vitamins and analogues thereof are preferred active ingredients of the present invention. As used herein, "vitamins" include vitamins such as vitamin A, $B_1$, $B_2$, $B_3$, $B_5$, $B_6$, $B_7$, $B_9$, $B_{12}$, C, $D_1$, $D_2$, $D_3$, $D_4$, and K.

Vitamin $D_3$ promotes the body's absorption of calcium, which is essential for the normal development and maintenance of healthy teeth and bones. Calcium is also important to nerve cells, including the brain. Vitamin $D_3$ is essential for calcium and phosphorus homeostasis in the blood. Vitamin $D_3$ deficiency can lead to osteoporosis in adults or rickets in children. Excessive doses of Vitamin $D_3$ can result in increased calcium absorption from the intestinal tract, and increased calcium resorption from the bones, leading to elevated levels of calcium in the blood and urine. Elevated blood calcium may cause calcium deposition in soft tissues such as the heart and lungs, which can reduce their ability to function. Kidney stones, vomiting, and muscle weakness may also occur due to the ingestion of too much Vitamin $D_3$.

Unlike any other vitamin, Vitamin $D_3$ (cholecalciferol) is a prehormone. It is synthesized when light is absorbed by 7-dehydrocholesterol. In the liver, Vitamin $D_3$ is converted by the enzyme 25-hydroxylase into 25-hydroxy Vitamin $D_3$ (calcidiol). The body stores calcidiol in the blood and fat for later use. In the kidney, 25-hydroxy Vitamin $D_3$ serves as a substrate for 1-alpha-hydroxylase, yielding 1,25-dihydroxy Vitamin $D_3$ (calcitriol), the biologically active form of Vitamin $D_3$ (Scheme 1).

Scheme 1: Synthesis of Vitamin $D_3$ and Conversion Into Its Active Form Calcitriol.

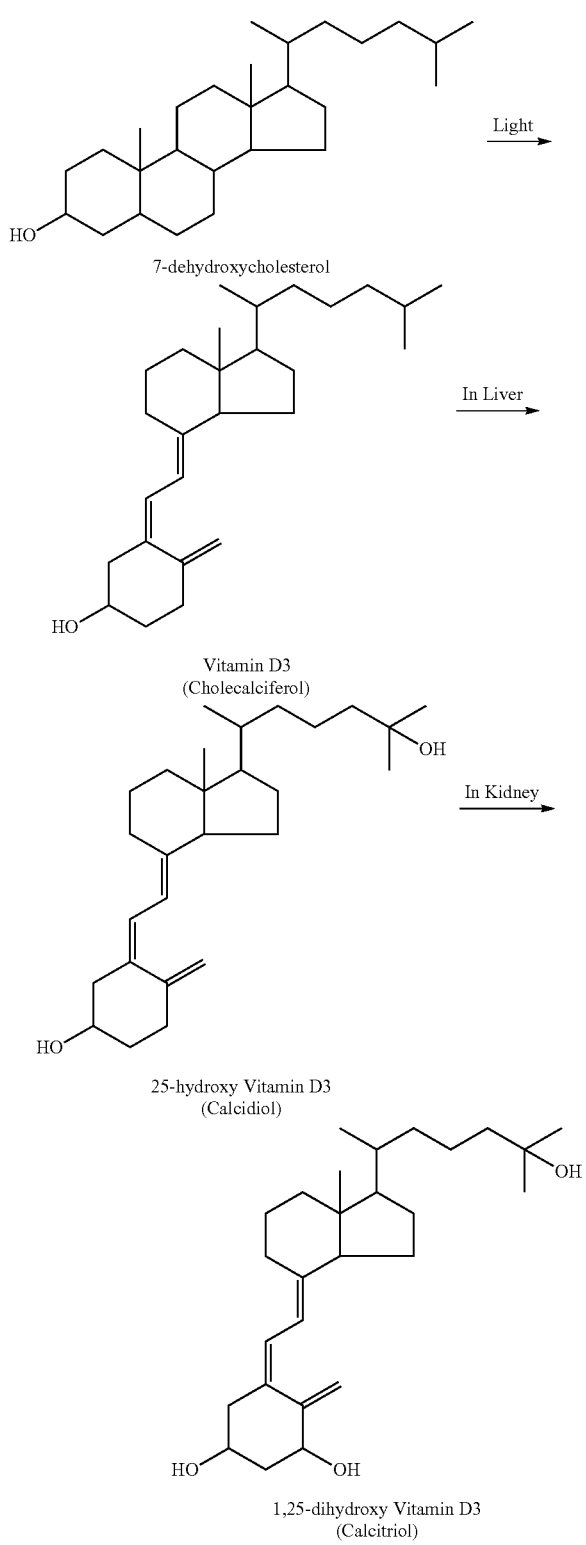

Vitamin $D_3$ regulates proliferation and differentiation as well as immune response. Many cell types in the skin have Vitamin $D_3$ receptors, including keratinocytes and lymphocytes. Calcipotriene and calcitriol have equivalent affinities for these receptors. Like calcitriol, calcipotriene inhibits proliferation and induces the differentiation of normal and malignant keratinocytes in culture (Guilhou, J. J. *Ann Dermatol Venereol* 128:229-37 (2001); Binderup, L. et al., *Rev Contemp Pharmacother* 3:357-65 (1992)). Vitamin $D_3$ has also been shown to induce normal differentiation in neoplastic epidermis reconstructed from transfected keratinocytes, thus confirming potential anti-neoplasic effects of Vitamin $D_3$ (Mils, V. et al., *J Investig Dermatol Symp Proc* 1:87-93 (1996)).

Calcipotriene (also known as calcipotriol, (5Z,7E,22E,24S)-24-cyclopropyl-9,10-secochola-5,7,10(19), 22 tetraene-1α,3β,24-triol) is a synthetic analog of Vitamin $D_3$. It was first synthesized by Leo Pharma, Denmark, in 1985. Topical calcipotriene has been on the market in Europe since 1992, and in the US since 1993. There are three topical calcipotriene dosage forms on the market in the US: an ointment, for once or twice-daily use to treat plaque psoriasis in adults; a cream, for twice-daily use to treat plaque psoriasis; and a solution, for twice-daily use to treat chronic, moderately severe psoriasis of the scalp. All three products contain calcipotriene at a concentration of 0.005%.

The effectiveness of topical calcipotriene in the treatment of psoriasis results mainly from inhibition of epidermal proliferation and stimulation of differentiation of epidermal cells. In addition, calcipotriene increases the number of Vitamin $D_3$ receptors in epidermal nuclei (Reichrath, J. et al., *J Am Acad Dermatol* 36:19-28 (1997)). The chemical structure of calcipotriene is provided below.

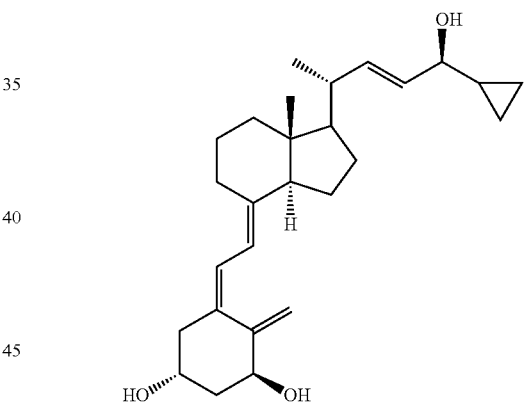

Although calcitriol has been shown to induce cell differentiation and inhibit cell proliferation, its use as an antipsoriatic agent is limited because of its potent effect on calcium metabolism. Calcipotriene, on the other hand, has 100-200 times lower calcemic potency, while inducing cell differentiation and inhibiting cell proliferation at concentrations similar to calcitriol. This lead to the development of calcipotriene as a therapeutic alternative in the topical treatment of psoriasis (Binderup, L. et al., *Rev Contemp Pharmacother* 3:357-65 (1992); Binderup, L. *Pharmacol Toxicol* 72:240-4 (1993); Knutson, J. C. et al., *Biochem Pharmacol* 53:829-37 (1997); Kragballe, K. *Pharmacol Toxicol* 77:241-6 (1995)).

As used herein, "vitamin analogue" includes compounds that are derived from a particular vitamin, and thus are similar in structure and have similar chemical and physiological properties. Vitamin analogues useful in the present invention include naturally occurring and synthetic analogues. Vitamin analogues of the present invention include, but are not limited to, calcidiol, calcitriol, calcipotriene, paricalcitol, 22-oxacalcitriol, dihydrotachysterol, calciferol, and those listed in U.S. Pat. No. 6,787,529. Vitamin A analogues useful in the present invention include, but are not limited to, acitretin, retinaldehyde, retinoic acid, dehydroretinol, fenretinide, hydroxyretroretinol, didehydroretinoic acid, carotenes, tretinoin and its isomers. One of skill in the art will appreciate that other vitamin analogues are useful in the present invention.

The pharmaceutically active ingredient may be present in any effective amount. The pharmaceutically active ingredient may be present in amounts of less than 0.005%, or approximately 0.005% by weight to approximately 10% by weight, preferably approximately 0.05% to approximately 1% by weight, based on the total weight of the pharmaceutical aerosol foam composition.

In certain aspects, the aerosol foam base can be made using compositions that are well known in the art. For example, admixtures of long chain alcohols and emulsifiers are typical components of the foam base. The foam can be a quick-breaking foam, or a foam which collapses more slowly.

The pharmaceutical aerosol foam composition may further include an effective amount of an aerosol propellant. As used herein, the term "aerosol propellant" refers to a gas that assists in propelling the foamable composition out of a pressurized container. The aerosol propellant can be any suitable gas or mixture thereof, such as a hydrocarbon, a chlorofluorocarbon, dimethyl ether, hydrofluorocarbons and a mixture thereof. Hydrocarbon propellants include, but are not limited to, propane, n-butane and isobutane. Chlorofluorocarbons are alkanes where all the hydrogens have been replaced with chlorine and fluorine atoms. Exemplary chlorofluorocarbons include, but are not limited to, chlorofluoromethanes such as trichlorofluoromethane and dichlorodifluoromethane, and chlorofluoroethanes such as trichlorotrifluoroethane. Hydrofluorocarbons are alkanes where some hydrogens have been replaced with fluorine atoms, but some hydrogen atoms remain. Exemplary hydrofluorocarbons include, but are not limited to, hydrofluoromethanes such as trifluoromethane, and hydrofluoroethanes such as tetrafluoroethane.

In a preferred embodiment the aerosol propellant is a hydrocarbon. Where the aerosol propellant is a hydrocarbon it may be present in an amount of from approximately 2.5% to 20% by weight, preferably 2.5% to 7.5% by weight, based on the total weight of the pharmaceutical mousse composition. The propellant may be introduced into the mousse composition at the time of filling utilizing for example, a standard aerosol dispenser, e.g. a spray can arrangement. One of skill in the art will appreciate that other aerosol propellants are useful in the present invention.

The occlusive agent utilized according to the present invention may be any excipient or combination thereof that provides an occlusive layer or hydration barrier to the skin. An occlusive layer or hydration barrier is a layer or barrier sufficient to result in reduction in transepidermal water loss, which results in skin hydration. Suitable occlusive agents may be selected from one or more of the group consisting of mineral oils and greases, long chain acids, animal fats and greases, vegetable fats and greases, water insoluble polymers and the like. In a preferred embodiment the occlusive agent is petrolatum.

The occlusive agent is present in an amount sufficient to permit the formation of an occlusive layer or hydration barrier on the skin of the patient. Surprisingly, applicants have discovered it is possible to form such an occlusive layer with a relatively low amount of occlusive agent. For example the amount of occlusive agent in the mousse composition may be up to approximately 55%, preferably approximately 40% or less by weight based on the total weight of the composition. In a preferred embodiment, the amount of occlusive agent in the mousse composition may be up to approximately 50%, more preferably from approximately 20 to 50% by weight. In certain other embodiments, the amount of occlusive agent is up to 20% by weight, such as 1% to 20% for example, 1%, 2%, 3%, 4%, 5%, 6%, 7%, 8%, 9%, 10%, 11%, 12%, 13%, 14%, 15%, 16%, 17%, 18%, 19%, or 20%. In other embodiments, the occlusive agent is present in an amount of about 20%, 25%, 30%, 35%, 40%, 45% and 50%.

The pharmaceutical mousse composition may further include an effective amount of an emulsifier and/or surfactant. The emulsifier or surfactant may be selected from one or more of the group consisting of non-ionic, anionic and cationic surfactants, e.g. fatty alcohols, fatty acids and fatty acid salts.

Surfactants useful in the present invention include, but are not limited to, a non-ionic surfactant, a cationic surfactant, an anionic surfactant, an amphoteric surfactant, an ampholytic surfactant, a fatty alcohol, a fatty acid and fatty acid salts thereof. A surfactant's hydrophilic/lipophilic balance (HLB) describes the surfactant's affinity toward water or oil (1-20, with 1 being lipophilic and 20 being hydrophilic). The HLB of a blend of two surfactants equals the weight fraction of surfactant A times its HLB value plus the weight fraction of surfactant B times its HLB value (weighted average). According to one or more embodiments of the present invention, the surface-active agent has a hydrophilic lipophilic balance (HLB) between about 9 and about 14, for example, 9, 10, 11, 12, 13, and 14, which is the preferred HLB (a HLB preferred to stabilize an o/w emulsion of a given oil) of most oils and hydrophobic solvents. One of skill in the art will appreciate that other surfactants are useful in the present invention.

As used herein, the term "fatty acid" include a carboxylic acid having an aliphatic tail, typically from 4 to 30 carbon atoms long. Fatty acids can be saturated, mono-unsaturated or poly-unsaturated. Examples of fatty acids useful in the present invention, include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). One of skill in the art will appreciate that other fatty acids are useful in the present invention.

In certain preferred aspects, the compositions of the present invention are oil-in-water emulsions. Generally, a preparation of one liquid distributed in small globules throughout the a second liquid is an emulsion. The dispersed liquid is the discontinuous phase, whereas the dispersion medium is the continuous phase. When the oil phase is the dispersed liquid and the aqueous solution is the continuous phase, typically the emulsion is known as an oil-in-water emulsion.

Examples of suitable non-ionic surfactants include glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, and the like.

As used herein, the term "fatty alcohol derivative" includes a fatty alcohol compound that has been modified by one or several chemical reactions. For example, the alcohol can be oxidized to a carbonyl compound such as an aldehyde or carboxylic acid. In addition, the alcohol can be protected with a suitable protecting group known to one of skill in the art. Other derivatives can include esters or ethers formed using a fatty alcohol, such as a polyoxyethylene fatty alcohol ether. Polyoxyethylene fatty alcohol ethers useful in the present invention include, but are not limited to, polyoxyl 20 cetostearyl ether and polyoxyl 10 oleyl ether, where the number refers to the average number of polyoxyethylene units in the polymer chain. One of skill in the art will appreciate that other fatty alcohol derivatives are useful in the present invention.

Examples of suitable anionic surfactants are soaps including alkali soaps, such as sodium, potassium and ammonium salts of aliphatic carboxylic acids, usually fatty acids, such as sodium stearate. Organic amine soaps, also included, include organic amine salts of aliphatic carboxylic acids, usually fatty acids, such as triethanolamine stearate. Another class of suitable soaps is the metallic soaps, salts of polyvalent metals and aliphatic carboxylic acids, usually fatty acids, such as aluminum stearate. Other classes of suitable anionic surfactants include sulfated fatty acid alcohols such as sodium lauryl sulfate, sulfated oils such as the sulfuric ester of ricinoleic acid disodium salt, and sulfonated compounds such as alkyl sulfonates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sulfonate such as aryl naphthalene with alkyl substitutes. Examples of suitable cationic surfactants include amine salts such as octadecyl ammonium chloride, quarternary ammonium compounds such as benzalkonium chloride.

Surfactant combinations such as for example, sorbitan monostearate and polysorbate 60 are suitable for use in the present invention.

The emulsifier component may be present in any suitable stabilizing amount. Preferably, the emulsifier component may be in an amount where the ratio of emulsifier component to the occlusive agent, active pharmaceutical ingredient and cosolvent is about 1:3, 1:4, 1:5, 1:6, 1:7, 1:8, 1:9 and 1:10. The emulsifier component may be present in an amount of from approximately 1% to 15% by weight, preferably approximately 2.0% to 5.0% by weight, based on the total weight of the pharmaceutical mousse composition.

The aqueous solvent may be present in an amount of from approximately 25% to 95% by weight, preferably approximately 70% to 85% by weight, such as 70%, 71%, 72%, 73%, 74%, 75%, 76%, 77%, 78%, 79%, 80%, 81%, 82%, 83%, 84%, or 85%, based on the total weight of the pharmaceutical mousse composition. In other embodiments, water is present in an amount from about 40% to about 60%. In still other embodiments, water is present in an amount from about 70% to about 90%.

The compositions may further include an organic cosolvent. The organic solvent may be an ester of a fatty acid for example a C12-C15 alkyl benzoate, a medium to long chain alcohol, an aromatic and/or alkyl pyrollidinone, an aromatic and/or alkyl, and/or cyclic ketone, an aromatic and/or alkyl, and/or cyclic ether, substituted and/or unsubstituted single or multiple ring aromatic, straight chain and/or branched chain and/or cyclic alkane or silicone. The organic cosolvent may be present in amounts of approximately 0.25% to 50% by weight, preferably 0.5 to 2% by weight, based on the total weight of the pharmaceutical mousse composition. Preferred organic cosolvents include C12-C15 alkyl benzoates (FINSOLV TN) and caprylic/capric triglyceride (CRODAMOL GTCC).

As used herein, the term "humectant" includes an agent that absorbs water from the air. Humectants are characterized as having several hydrophilic functional groups. Humectants useful in the foamable composition of the present invention include, but are not limited to, propylene glycol and polyols such as sorbitol, maltitol glycerine, glyceryl triacetate, polydextrose and other polyols such as polymeric polyols including polydextrose. When a humectant is present, it is present in an amount of from about 1% to about 20% by weight. In some embodiments, the humectant is present in an amount of from about 5% to about 15% by weight. One of skill in the art will appreciate that other humectants, and amounts, are useful in the present invention.

As used herein, the term "stabilizing" includes maintaining a compound in a specific state and preventing or slowing fluctuations from that particular state into another. In the present invention, it is preferable to stabilize an oil soluble vitamin or vitamin derivative in water by the use of a stabilizer such as a water soluble polymer. Other stabilizers are known to one of skill in the art.

As used herein, the terms "stabilizer," or "preservative" include an agent that prevents the oxidation of other compounds. Examples of preservatives useful in the compositions of the present invention include, but are not limited to, an antioxidant, sodium nitrate, sodium nitrite, sulfites, (sulfur dioxide, sodium bisulfate, potassium hydrogen sulfate, and the like), disodium EDTA, formaldehyde, glutaraldehyde, diatomaceous earth, ethanol, dimethyl dicarbonate, methylchloroisothiazolinone, beta-carotene, selenium, coenzyme Q10 (ubiquinone), lutein, tocotrienols, soy isoflavones, S-adenosylmethionine, glutathione, taurine, N-acetylcysteine, Vitamin E (alpha-tocopherol), Vitamin E derivatives such as tocopherol acetate and tocopherol palmitate, Vitamin C and its derivatives, alpha-lipoic acid, 1-carnitine, phenoxyethanol, butylated hydroxytoluene and sodium benzoate. One of skill in the art will appreciate that other preservatives are useful in the present invention. When a preservative is present, it is typically present in an amount of from about 0.1% to about 5% by weight.

Other stabilizers useful in the present invention include complexing agents such as edetate disodium, dihydrate. When a complexing agent is present, it is present in an amount of from about 0.001% to about 1%. One of skill in the art will appreciate that other complexing agents, and amounts, are useful in the present invention.

The pharmaceutical mousse composition according to the present invention may also contain other non-essential ingredients. The composition may contain up to 10 weight percent of conventional pharmaceutical adjuvants. These adjuvants or additives include preservatives, stabilizers, antioxidants, pH adjusting agents, skin penetration enhancers (lie propylene glycol), and viscosity modifying agents.

A. Topical Emulsion Compositions

In one embodiment, the present invention provides a topical oil-in-water emulsion comprising a vitamin or analogue thereof, wherein the vitamin or analogue thereof is solubilized in the water phase (continuous phase) and a stabilizer is solubilized in the oil phase (discontinous phase). In certain aspects, the emulsion of the present invention further comprises an emulsifier and an occlusive agent. The compositions of the present invention can be housed in a pressurized container, such that the composition is a foam when released from the pressurized container. Alternatively, the compositions of the present invention can be a lotion, cream, ointment, solution, gel, paste, or applied via a dermal patch.

In certain preferred aspects, the vitamin or analogue of the present invention is selected from the group consisting of vitamin A, $B_1$, $B_2$, $B_3$, $B_5$, $B_6$, $B_7$, $B_9$, $B_{12}$, C, $D_1$, $D_2$, $D_3$, $D_4$, and K and an analogue thereof. Preferred vitamins include vitamins A and $D_1$, $D_2$, $D_3$, and $D_4$ and their analogues. Vitamin A analogues useful in the aerosol compositions of the present invention include, but are not limited to, acitretin, retinol, retinaldehyde, retinoic acid, dehydroretinol, fenretinide, tazarotene, tretinoin and its isomers, and carotenes. In some embodiments, the vitamins or analogues of the present invention are vitamin D or vitamin D analogues including, but not limited to, calcidiol, calcitriol, calcipotriene and those listed in U.S. Pat. No. 6,787,529. In other embodiments, the vitamin D or analogue is calcipotriene. The vitamins or analogues can be anhydrous, or a hydrate, such as calcipotriene anhydrate or monohydrate (U.S. Pat. No. 5,763,426). Other hydrates such as dihydrate and trihydrate are also useful. One of skill in the art will appreciate that other vitamins or vitamin analogues are useful in the present invention.

In some aerosol compositions of the present invention, the vitamin or analogue is present in amounts from approximately 0.0001% by weight to approximately 10% by weight, based on the total weight of the aerosol composition. In other aerosol compositions, the vitamin or analogue is present in amounts from approximately 0.001% to approximately 1% by weight. In still other aerosol compositions, the vitamin or analogue is present in amounts from approximately 0.001% to approximately 0.1% by weight. In yet another aerosol composition, the vitamin or analogue is present in amounts from approximately 0.001% to approximately 0.01% by weight. One of skill in the art will appreciate that aerosol compositions having other amounts of the vitamin or analogue are useful in the present invention.

In certain aspects, vitamins useful in the present invention are oil soluble. The vitamins of the present invention can be dissolved in water via first dissolving in a water soluble solvent (e.g., organic solvent) such as propylene glycol. Other solvents having miscibility with both polar and non-polar substances can also be used including for example, diols such as ethylene glycol, butylene glycol and other polyols. The mixture of water soluble organic solvent and vitamin is then added to the water where the water soluble polymer maintains the vitamin in a solution state. Other solvents having miscibility with both polar and non-polar substances can also be used including; polyols, for example PEG 200, PEG 300, PEG 400 and PEG 800; and ethers, for example, ethylene glycol monoethyl ether and diethylene glycol monoethyl ether; and esters, for example ethyl acetate and propylene carbonate; and heterocyclic compounds, for example n-methylpyrrolidone. For particular agents (e.g., tretinoin), alcohols are useful, such as ethanol, n-propanol, isopropanol, n-butanol and t-butanol. Other water soluble organic solvents useful in the present invention are known to one of skill in the art.

The medium to long chain alcohols described above for the organic cosolvent include fatty alcohols and fatty alcohol derivatives. Fatty alcohols useful as the organic cosolvent include, but are not limited to, capryl alcohol (C8), pelargonic alcohol (C9), capric alcohol (C10), lauryl alcohol (C12), myristyl alcohol (C14), cetyl alcohol (C16), palmitoleyl alcohol (C16), stearyl alcohol (C18), isostearyl alcohol (C18), elaidyl alcohol (C18), oleyl alcohol (C18), linoleyl alcohol (C18), elaidolinoleyl alcohol (C18), linolenyl alcohol (C18), ricinoleyl alcohol (C18), arachidyl alcohol (C20), behenyl alcohol (C22), erucyl alcohol (C22), lignoceryl alcohol (C24), ceryl alcohol (C26), montanyl alcohol/cluytyl alcohol (C28), myricyl alcohol/melissyl alcohol (C30) and geddyl alcohol (C34). In some embodiments, the organic cosolvent of the aerosol composition of the present invention is at least one $C_{14}$-$C_{22}$ alcohol. In other embodiments, the organic cosolvent is a C16 alcohol, a C18 alcohol, or a combination. In still other embodiments, the organic cosolvent is a mixture of cetyl alcohol and stearyl alcohol.

In certain aspects, the fatty alcohols of the present invention can be present in an amount from about 0.1% to about 5% w/w. One of skill in the art will appreciate that other amounts of the fatty alcohol are useful in the present invention.

The surfactant of the aerosol composition of the present invention can be a single surfactant or a mixture of several different surfactants. In one embodiment, the aerosol composition of the present invention comprises an surfactant comprising a mixture of a $C_{14}$-$C_{22}$ alcohol, a sorbitan ester and a polyoxyethylene fatty alcohol ether. In another aspect, the surfactant comprises a mixture of a $C_{14}$-$C_{22}$ alcohol and a polyoxyethylene fatty alcohol ether. One of skill in the art will appreciate that other surfactants, and mixtures thereof, are useful in the present invention.

In some embodiments, the $C_{14}$-$C_{22}$ alcohol can be cetyl alcohol, stearyl alcohol, or a mixture thereof. In other embodiments, the $C_{14}$-$C_{22}$ alcohol can be cetyl alcohol. One of skill in the art will appreciate that other alcohols are useful in the present invention.

The surfactant of the aerosol composition of the present invention can be present in any suitable stabilizing amount. In one embodiment, the surfactant is present in an amount of from approximately 0.1 to 15% by weight, based on the total weight of the composition. In other embodiments, the surfactant is present in an amount of approximately 0.1% to about 10% by weight. One of skill in the art will appreciate that other amounts of surfactant are useful in the present invention.

In certain aspects, the non-ionic surfactant of the aerosol composition of the present invention (i.e., the sorbitan ester or polyoxyethylene fatty alcohol ether) can be present in an amount from about 1% to about 15% w/w. The non-ionic surfactant can also be present in an amount from about 3% to about 8% w/w. One of skill in the art will appreciate that other amounts of non-ionic surfactant are useful in the present invention.

The aerosol compositions of the present invention can also comprise additional adjuvants, as noted above, such as preservatives, stabilizers, pH adjusting agents, and skin penetration enhancers.

The pH adjusting agents of the present invention are compounds or mixtures that can adjust the pH of a solution to make the solution more acidic or more basic. In some embodiments, the compositions of the present invention include a buffering agent as the pH adjusting agent in order to maintain the pH at a desired point. Buffering agents useful in the present invention include organic and inorganic acids and bases such as sodium hydroxide, dibasic sodium phosphate anhydrous, and mixtures thereof. In some embodiments, the buffering agent is sodium hydroxide. In other embodiments, the buffering agent is dibasic sodium phosphate anhydrous. In a further embodiment, the buffering agent is a mixture of sodium hydroxide and dibasic sodium phosphate anhydrous. One of skill in the art will appreciate that other buffering agents are useful in the present invention.

In another embodiment, the pH of the aerosol composition is from about pH 4.0 to about pH 9.0, such as 4.0, 5.0, 6.0, 7.0, 8.0, 9.0. In other embodiments, the pH is from about pH 7.0 to about pH 9.0. One of skill in the art will appreciate that other pHs of the aerosol composition are useful in the present invention.

When a buffering agent is present, it is present in an amount of about 0.001% to about 1.0% by weight, such as 0.01-0.5%. One of skill in the art will appreciate that other amounts of buffering agent are useful in the present invention.

Viscosity modifying agents of the present invention include viscosity reducers, or compounds or mixtures that increase the viscosity of a mixture. Suitable viscosity reducers include for example, isopropyl myristate. Suitable viscosity reducers include other esters, for example, C12-C15 alkyl benzoate, caprylic/capric triglyceride, myristyl lactate, benzyl benzoate and isopropyl palmitate. Suitable agents to increase viscosity include gelling agents such as Carbopol 934®, Carbopol 940®, Carbopol 950®, Carbopol 980®, Carbopol 951® and Carbopol 981®. Other agents to increase viscosity include for example, gums and polysaccharides, for example, gellan gum, guar gum, karaya gum, locust-bean gum, xanthan gum, natural gum, chitosan, hyaluronic acid and salts thereof; and, proteins, for example gelatin. When a viscosity modifier is present, it is present in an amount of about 0.1% to about 20%, preferably about 0.1% to about 5% by weight. One of skill in the art will appreciate that other viscosity modifiers and amounts, are useful in the present invention.

B. Enhanced Active Agent Stability Via Presence of Tocopherol and Derivatives Thereof 1. Calcipotriene Calcipotriene forms an equilibrium with pre-calcipotriene, which reduces the amount of calcipotriene present in a pharmaceutical composition, as well as reducing the efficacy of the composition. The addition of stabilizers and preservatives in the water-in-oil emulsions of the present invention assist in preventing the degradation of the active agent. Unexpectedly, the present formulation affords enhanced stability with the addition of a stabilizer such as tocopherol or a tocopherol derivative in one phase (the oil phase), with the active vitamin or analogue thereof (e.g., calcipotriene) in the other phase (water phase). The unexpected advantageous nature of the present invention is due in-part to the added stability afforded by the stabilizer (e.g., tocopherol or a tocopherol derivative) even though the stabilizer is added to a completely different phase. Prior to the advent of the present invention, it was believed that in order to be effective, a stabilizer must be added to the phase where the active ingredient is dissolved. The formulations of the present invention possess enhanced stability despite the addition of a stabilizer to a phase other than that where the active ingredient is dissolved.

2. Tretinoin

Another vitamin analogue useful in the present invention is tretinoin. Chemically, tretinoin is all-trans-retinoic acid, also known as (all-E)-3,7-dimethyl-9-(2,6,6-trimethyl-1-cyclohexen-1-yl)-2,4,6,8-nonatetraenoic acid. Tretinoin is a member of the retinoid family of compounds, and is a metabolite of naturally occurring Vitamin A. Tretinoin has a molecular weight of 300.44. Tretinoin has the following structure:

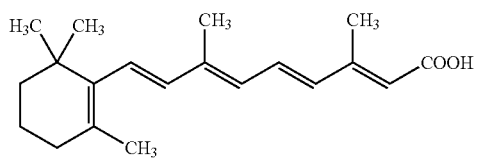 [SMILES: CC1=C(/C=C/C(C)=C/C=C/C(C)=C/C(=O)O)C(C)(C)CCC1]

Although the exact mode of action of tretinoin is unknown, current evidence suggests that topical tretinoin decreases cohesiveness of follicular epithelial cells with decreased microcomedo formation. Additionally, tretinoin stimulates mitotic activity and increased turnover of follicular epithelial cells causing extrusion of the comedones.

Tretinoin is known to be unstable in the presence of oxidizing agents and sunlight. (see, for example, Martin B, et al., *Br J Dermatol*. 1998; 139 (suppl 52):8-11. In order to increase stability, a stabilizer such as tocopherol or a derivative thereof is added to the composition.

3. Acitretin

In yet a further aspect, acitretin is a vitamin analogue useful in the present invention. Chemically, acitretin is all-trans-9-(4-methoxy-2,3,6-trimethylphenyl)-3,7-dimethyl-2,4,6,8-nonatetraenoic acid (a retinoid). Acitretin is a metabolite of etretinate and is related to both retinoic acid and retinol (vitamin A). It is a yellow to greenish-yellow powder with a molecular weight of 326.44. The structural formula is:

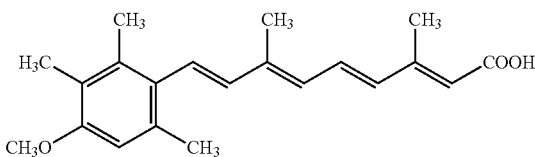

Acitretin is a form of vitamin A. The exact way that acitretin works is unknown. Acitretin is used to treat severe psoriasis that has not responded to other treatments. In order to increase stability of acitretin, a stabilizer such as tocopherol or a derivative thereof is added to the formulation.

In certain aspects, the phenolic hydroxyl group of a stabilizer (e.g., tocopherol) is responsible for the antioxidant properties. Upon contact with a free radical, the hydrogen of the phenolic hydroxyl group of tocopherol is donated to the free radical entity, creating a tocopherol free radical that is stabilized through resonance. Without being bound to any particular theory, the combination of tocopherol provides additional stability for a vitamin or an analogue thereof (e.g., calcipotriene) that other combinations of antioxidants and preservatives do not provide. The additional stability afforded by the combination of tocopherol is not fully attributable to the antioxidant properties of the phenolic hydroxyl group, however. Additional stability for the vitamin or analogue thereof (e.g., calcipotriene) is derived from tocopherol as a whole. In addition to the phenolic moiety, tocopherol comprises a fused pyran moiety forming a benzopyran, as well as a branched C13-alkyl chain pendant to the pyran moiety. It is believed that the combination of the phenolic moiety, the benzopyran and the branched C13-alkyl chain impart additional stability to the composition that cannot be obtained through the use of other antioxidants.

For example, it was determined that a loss of potency in calicipotriene formulations not having a stabilizer such as tocopherol was due to calcipotriene degradation. A major degradation product in the formulations not having tocopherol was trans-calcipotriene. Trans-calcipotriene is not an oxidation by-product. That is, trans-calcipotriene is not generated by oxidizing calcipotriene. Therefore, a stabilizer acting solely as an antioxidant would not be expected to decrease or retard the amount of trans-calcipotriene. As such, tocopherol is believed to be playing a stabilizing role in addition to its role as an antioxidant, possibly by preventing or reducing the amount of isomerization by-product.

Other stabilizers useful to practice the invention include for example, superoxide dismutase, beta-carotene, BHT (butylated hydroxytoluene), BHA (butylated hydroxyanisole) and coenzyme Q10. The antioxidant providing added stability can be present in a ratio of active agent to antioxidant of from 10:1 to 1000:1, such as 10:1 to 750:1, 10:1 to 500:1 and 10:1 to 100:1.

C. Methods of Treating

In other embodiments, the present invention includes a method for treating a dermatological disorder in a mammal comprising administering a topical emulsion composition of the present invention, wherein the composition is a foam when released from a pressurized container, to treat the dermatological disorder.

As used herein, the term "treating" includes any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination. For example, the methods of the invention selectively treat acne vulgaris and/or psoriasis by diminishing of symptoms of these indications.

Dermatological disorders that are treatable by the methods of the present invention include, but are not limited to, dermatological conditions linked to disorders of keratinization involving differentiation and proliferation, in particular, acne vulgaris, comedonic or polymorphic acne, nodulocystic acne, acne conglobata, senile acne and secondary acnes such as solar, drug or occupational acne; for other types of keratinization disorders especially ichthyoses, ichthyosiform conditions, Darier's disease, palmoplantar keratoderma, leukoplakia and luecoplakiform conditions or lichen and lichen planus; dermatological disorders having an inflammatory or immunoallergic component, in particular, all forms of psoriases, either cutaneous, mucosal or ungual, and psoriatic rheumatism, and cutaneous atopy such as eczema or respiratory atopy, dry skin, inflammation of the skin, solar erythema, skin allergies or other skin disorders of the epidermis and dermis. The present invention contemplates the treatment of skin disorders of humans and animals. In some embodiments, the dermatological disorder treated by the methods of the present invention is psoriasis. One of skill in the art will appreciate that other dermatological disorders are useful in the present invention.

D. Methods of Stabilizing

In other embodiments, the present invention provides a method for stabilizing a vitamin or an analogue thereof in a topical emulsion composition, comprising a first step of providing a vitamin or analogue thereof, wherein the vitamin or analogue thereof is solubilized in the water phase. The methods of the present invention for stabilizing a vitamin or an analogue thereof in a topical emulsion composition further comprises a second step comprising providing a stabilizer solubilized in the oil phase, wherein the vitamin or analogue thereof is stabilized by the presence of the stabilizer even though, surprisingly the stabilizer is present in a different phase. The methods for stabilizing the active vitamin or analogue thereof are thus, contrary to conventional formulation wisdom and completely unexpected.

II. Examples

The present invention will now be more fully described with reference to the accompanying figures and examples. It should be understood that the description following is illustrative only and should not be taken in any way as restrictive on the generality of the foregoing description.

Example 1

Formulations

A series of 7 pharmaceutical formulations were prepared in accordance with the present invention. The composition of each formulation is given in Table 1.

TABLE 1

| Ingredient | 1 | 2 | 3 | 4 | 5 | 6 | 7 |
|---|---|---|---|---|---|---|---|
| Petrolatum | 10% | 10% | 20% | 30% | 30% | 40% | 50% |
| Clobetasol Propionate | 0.05% | 0.05% | 0.05% | 0.05% | 0.05% | 0.05% | 0.05% |
| Caprylic/Capric Triglyceride | — | — | — | — | 10% | — | — |
| Alkyl Benzoate | 10% | 10% | 10% | 10% | — | 10% | 10% |
| Cetearyl glucoside | 2.5% | — | — | — | — | — | — |
| Sorbitan Stearate | — | 1.63% | 2.54% | 3.44% | 3.02% | 4.35% | 5.25% |
| Polysorbate 60 | — | 2.37% | 3.46% | 4.56% | 4.98% | 5.65% | 6.75% |
| Water | 72.25% | 70.95% | 58.95% | 46.95% | 46.95% | 34.95% | 22.95% |
| Preservatives | 0.2% | — | — | — | — | — | — |
| Propellant | 5% | 5% | 5% | 5% | 5% | 5% | 5% |

Example 2

Effect of Petrolatum Concentration on the In-Vitro Epidermal Penetration of Clobetasol from Topical Mousse Formulations Aim.

The aim of the study was to:

I. determine the penetration of the steroid clobetasol into human epidermis following topical application of mousse formulations to which increasing concentrations of petrolatum had been included as a potential occlusive agent and penetration enhancer.

II. To assess clobetasol penetration following application to intact epidermis and that which had been stripped 3 times with tape to model the impaired stratum corneum barrier function seen in the dermatological conditions for which the drug is used clinically.

Method.

Preparation of Epidermal Membranes:

Donated human female abdominal skin was separated by blunt dissection, to remove subcutaneous fat and extraneous tissue, and immersed in water at 60° C. for 2 minutes to allow separation of the epidermal-dermal junction. Epidermal membranes were lifted from the dermis by gently rolling from one end with the fingers and stored on filter paper, stratum corneum uppermost, at −20° C. until use.

Diffusion Studies

Epidermal membranes were mounted, stratum corneum uppermost and facing the donor chamber, on filter paper between the two halves of standard horizontal glass Franz-type diffusion cells (area approx. 1.3 cm$^2$). The bottom half of the diffusion cells was filled with approximately 3.5 ml of receptor medium (either 20% ethanol in distilled water for intact epidermal membrane studies or Baxter 20% Intralipid® solution for stripped skin studies) and continuously stirred with small magnetic stirring rod. Assembled cells were semi-submerged in a water bath maintained at 35±0.1° C.

Mousse formulations containing 0.05% clobetasol with the inclusion of 0, 30 or 50% petrolatum were gently applied to the donor chamber with a round-ended plastic rod which was wiped around the skin surface such that the skin was covered by a total dose of approximately 10 mg/cm$^2$. The weight of formulation applied was verified from the difference in weight of the application rod and small weigh boat from which the formulation had been applied before and after dosing.

Clobetasol was allowed to penetrate into the epidermis for 72 hrs. after which time the remaining formulation was removed from the skin surface by washing and a single tape strip was performed to ensure that minimal 'unpenetrated' material remained on the surface of the epidermis. All washes and tape strips were retained for quantification of clobetasol concentration. The area of epidermis exposed to the formulation was then removed from the membrane using a stainless steel punch which was cleaned with methanol between samples to avoid any cross contamination of clobetasol. Epidermal, tape and wash samples were all assayed for clobetasol concentration by high performance liquid chromatography.

Results.

FIG. 1 shows the fraction of the applied amount of clobetasol that was found to have penetrated into the epidermal membranes during the study. It can be clearly seen that inclusion of petrolatum in the mousse formulations has increased the amount of clobetasol penetrating into the epidermis of both intact and stripped skin samples. The recovery of the applied amounts of clobetasol in the washes, tape strip and epidermis was greater than 75% in all cases.

Conclusion.

Increasing concentrations of petrolatum in topical mousse formulations containing 0.05% clobetasol was able to increase the in-vitro human epidermal penetration of the steroid in both intact and stripped skin models.

Example 3

Preparation of an Aerosol Composition in a Pressurized Container

Calcipotriene Foam is an oil and water emulsion packaged in an aluminum container which is pressurized with a hydrocarbon (propane/butane) propellant.

Table 2 contains the list of materials, the quality standard and function of each material, the quantitative composition, and the formula for a batch size of 450 kg.

TABLE 2

Calcipotriene Foam 0.005% Quantitative Composition

| Component | Function | Percent (% w/w) |
|---|---|---|
| Calcipotriene | Active ingredient | 0.00552 |
| Cetyl alcohol | Emulsifier | 1.05 |
| Cyclomethicone | Viscosity reducer | 5.26 |
| Dibasic Sodium Phosphate Anhydrous | Buffering agent | 0.30 |
| Edetate Disodium, dehydrate | Complexing agent | 0.02 |
| Isopropyl Myristate | Viscosity reducer | 5.26 |
| Light Mineral Oil | Occlusive agent, viscosity reducer | 5.26 |
| Phenoxyethanol | Preservative | 0.50 |
| Polyoxyl 20 Cetostearyl Ether | Emulsifier | 5.26 |
| Propylene Glycol | Solvent, humectant | 10.53 |
| Purified Water | Solvent | 57.07448 |
| Sodium Hydroxide | Buffering agent | 0.01 |
| Sorbitan Monolaurate | Emulsifier | 4.21 |
| White Petrolatum | Occlusive agent | 5.26 |

Table 2 does not include the propellant. The propane/butane propellant is supplied as a blend of approximately 55% propane, 30% n-butane, and 15% isobutane. Typically the propellant is added at approximately 8 gram/100 grams of the formulation.

Description of Manufacturing and Packaging.

The manufacture of the drug product takes place in three primary steps: the oil phase, the water phase, and active phase. Any steps in which the calcipotriene is exposed to light are performed under red light to minimize potential degradation. Heat exposure is also minimized.

1. The required amounts of white petrolatum, light mineral oil, isopropyl myristate, sorbitan monolaurate, cetyl alcohol and phenoxyethanol are individually added into the primary compounding vessel at the initiation of the oil phase. While mixing, the oil phase is heated and the required amount of cyclomethicone is added. The ingredients are mixed until the solution is uniform.
2. The required amounts of purified water, edetate disodium dihydrate and sodium phosphate dibasic anhydrous are individually added into the water phase vessel at the initiation of the water phase. While mixing, the water phase is heated and the required amount of polyoxyl 20 cetostearyl ether is added. The ingredients are mixed until completely dissolved.
3. The required amounts of purified water and sodium hydroxide are individually added into the pH phase vessel at the initiation of the pH phase. The ingredients are mixed until completely dissolved.
4. The required amount of propylene glycol is added into the active phase vessel at the initiation of the active phase. While mixing, the required amount of calcipotriene is added. The active phase is heated and mixed until completely dissolved.
5. Approximately 70% of the water phase is added to the oil phase in the primary compounding vessel. The mixture is mixed and heated. The remainder (approximately 30%) of the water phase is cooled.
6. Contents in the primary compounding vessel are continuously mixed and slowly cooled.
7. The remainder of the water phase mixture (approximately 30%) is then added to the primary compounding vessel while being simultaneously cooled.
8. The pH phase is added to the mixture in the primary compounding vessel with continuous mixing.

9. The active phase is added to the mixture in the primary compounding vessel. The batch formulation mixture is continuously mixed and cooled.
10. The appropriate amount of the batch formulation is dispensed into each can.
11. The valve is placed onto the can then vacuum crimped.
12. The cans are then transported to a flame-proof gassing area where an appropriate amount of propellant (propane/butane) is injected into the can via the valve.
13. An actuator is applied and then a cover cap is placed on top of the can.

In step 4 of the above procedure, propylene glycol is added into the active phase. It is found that by adding the polyol in the active phase, a microemulsion or even sub micron emulsion is formed. In certain instances, it is possible to reproducibly manufacture sub micron particles at low temperature in the range 100-600 nm with the majority of particles being in the 100-200 nm range. The exclusion of propylene glycol from the initial water/oil phase mixing appears to allow the surfactants to pack into a microemulsion structure and with the assistance of temperature manipulation, to fix in place.

Example 4

Method of Treating Psoriasis Using a Vitamin D3 Analogue Foam Composition

An in vitro skin penetration study is used to compare skin permeation of calcipotriene from foam formulations, containing 0%, 10% or 20% propylene glycol, with that of an ointment formulation. This comparison allows insight into the relevance of the non-clinical and human pharmacokinetic data described in literature, with regards to the Foam formulations.

Healthy, human abdomen skin obtained within 24 hours of surgery, is dermatomed to a thickness of approximately 0.25 mm, and fitted into flow-through diffusion cells (Permegear Inc., Bethlehem, Pa.) with a 0.64 cm$^2$ exposure area. The cells are maintained at 37° C.±0.2° C. during the course of the experiment. Each test formulation is applied to skin sections at dose of 10 µL/0.64 cm$^2$, for 24 hours. The receptor fluid is pumped through the receptor chamber at a rate of –0.33 mL/h.

After 24-hours, the skin surface is washed by applying 20 µL of acetonitrile, wiped twice with tissue paper and stripped twice with transparent tape. The epidermis and dermis are heat separated by placing the skin on a heat block of 50° C. for 1.5 minutes. The washes, the tissue papers and tapes, the epidermis and dermis, and the receptor fluid, are all analyzed for drug content using HPLC.

This in vitro skin penetration model has proven to be a valuable tool to compare efficiency of topical formulations with respect to skin permeation and skin distribution profiles.

Example 5

Skin Penetration Study of Calcipotriene Cream Versus Inventive Foam composition

The results indicate that the inventive foam delivered measurable amounts of calcipotriene into the epidermis and dermis. Moreover, there is a correlation between the concentration of propylene glycol in the inventive formulation and the cumulative amount of calcipotriene in the skin. The low viscosity of the foam material advantageously improves spreading/absorption compared to the commercial cream. Further, the inventive formulation is non-crystalline and thus the active ingredient penetrates faster compared to the cream formulation.

Example 6

Comparative Example

Table 3 shows a comparison of various physical properties of an inventive embodiment compared to prior art formulations.

TABLE 3

| | | Products: | | | |
|---|---|---|---|---|---|
| | | (1) Emulsion (w/o) | (2) Solution | (3) Emulsion (o/w) | (4) Emulsion (o/w) |
| Description: | | Ointment Crystals dispersed in water phase Water phase dispersed in petrolatum →Crystal Dispersion →Ointment (largely anhydrous) →High viscosity →Greasy | Scalp Solution Crystals dissolved in IPA/water →Solution | Cream Monohydrate crystals dispersed in water Aqueous crystalline dispersion added to o/w cream → Crystal dispersion → Med-high viscosity | Inventive foam Crystals dissolved in w/miscible organic solvent Active solution added to o/w Submicron Emulsion Solution/colloidal solution →Low viscosity: Improved spreading/absorption Non-crystalline: No need to mill/Active penetrates faster |
| Contains Petrolatum: | | √ | X | √ | √ |
| Alcohol | | X | √(50%) | X | √(≤10%) |
| Actual Stinging? | | X | √ High levels cause stinging | X | X |

As is illustrated in Table 3, in comparing the inventive calcipotriene foam to calcipotriene ointment insofar as their occlusive properties are concerned (which leads to enhanced penetration), the foam and ointment are similar. However, the foam is far superior in that it is advantageously not greasy and cosmetically elegant. Further, in comparing the inventive calcipotriene foam to a calcipotriene scalp solution insofar as viscosity and spreadability are concerned, the vehicles are similar. However, the inventive foam advantageously does not contain large amounts of alcohol and therefore has reduced stinging on the skin.

Example 7

A. Calcipotriene Foam Formulation

TABLE 4

| Name | % w/w |
| --- | --- |
| $C_{16}$ alcohol | 1.00 |
| $C_{18}$ alcohol | 1.00 |
| Mineral Oil | 6.00 |
| Petrolatum | 1.00 |
| Isopropyl Myristate | 0.50 |
| Polyoxyl 20 Cetostearyl Ether | 2.50 |
| Vitamin E | 0.002 |
| Distilled Water | 77.853 |
| Edetate Disodium Dihydrate | 0.06 |
| Sodium Phosphate Dibasic, Anhydrous | 0.08 |
| Propylene Glycol | 10.0000 |
| Anhydrous Calcipotriene | 0.0050 |
| Total | 100.000 |
| Propellant (A70) | 7.88 |

B. Tretinoin Foam Formulation

TABLE 5

| Name | % w/w |
| --- | --- |
| $C_{16}$ alcohol | 1.00 |
| $C_{18}$ alcohol | 1.00 |
| Mineral Oil | 6.00 |
| Petrolatum | 1.00 |
| Isopropyl Myristate | 0.50 |
| Polyoxyl 20 Cetostearyl Ether | 2.50 |
| Vitamin E | 0.002 |
| Distilled Water | 82.808 |
| Edetate Disodium Dihydrate | 0.06 |
| Sodium Phosphate Dibasic, Anhydrous | 0.08 |
| Ethanol | 5.0000 |
| Tretinoin | 0.050 |
| Total | 100.000 |
| Propellant (A70) g/100 g | 8.00 |

C. Acitretin Foam Formulation

TABLE 6

| Name | % w/w |
| --- | --- |
| $C_{16}$ alcohol | 1.00 |
| $C_{18}$ alcohol | 1.00 |
| Mineral Oil | 6.00 |
| Petrolatum | 1.00 |
| Isopropyl Myristate | 0.50 |
| Polyoxyl 20 Cetostearyl Ether | 2.50 |
| Vitamin E | 0.002 |
| Distilled Water | 82.848 |
| Edetate Disodium Dihydrate | 0.06 |
| Sodium Phosphate Dibasic, Anhydrous | 0.08 |
| n-Methyl Pyrrolidone | 5.0000 |
| Acitretin | 0.010 |
| Total | 100.000 |
| Propellant (A70) g/100 g | 8.00 |

D. Description of Manufacturing Process

1. At ambient temperature, the required amounts of $C_{16}$ alcohol and $C_{18}$ alcohol light mineral oil, white petrolatum, isopropyl myristate, polyoxyl 20 cetostearyl ether and vitamin E are individually added into the primary compounding tank at the initiation of the oil phase.
2. While mixing, the oil phase is heated. The ingredients are mixed until the solution is uniform.
3. At ambient temperature, the required amounts of purified water, edetate disodium dihydrate and sodium phosphate dibasic anhydrous are individually added into the water phase stainless steel tank at the initiation of the water phase.
4. While mixing, the water phase is heated. The ingredients are mixed until completely dissolved.
5. At ambient temperature, the required amount of propylene glycol is added into the active phase stainless steel tank at the initiation of the active phase.
6. The active phase stainless steel tank is covered with black plastic. While mixing under yellow light, the propylene glycol is heated. While continuing to mix, the required amount of calcipotriene is added. The active phase is mixed until complete dissolution occurs.
7. The water phase is added to the oil phase in the primary compounding tank while mixing.
8. The contents in the primary compounding tank are mixed continuously.
9. The active phase is added into the mixture in the primary compounding tank. The bulk emulsion mixture is mixed continuously until a uniform mixture is obtained.
10. At ambient temperature, the appropriate amount of the bulk emulsion is dispensed into each can.

Example 8

Foam Formulations with Added Stability

In certain instances, the foam formulations of the present invention are substantially ethanol-free and substantially isopropanol-free formulations (e.g., lower than 5%). Unexpectedly, when added to the oil phase, alpha-tocopherol as a stabilizer yields increased stability and leads to less calcipotriene degradation than other stabilizers. The emulsions of the present invention truly possess surprising unexpected advantages in that the calcipotriene and the stabilizer are added to different phases. The emulsion enables increased enhanced stability not possible with prior art formulations.

Figure 5:
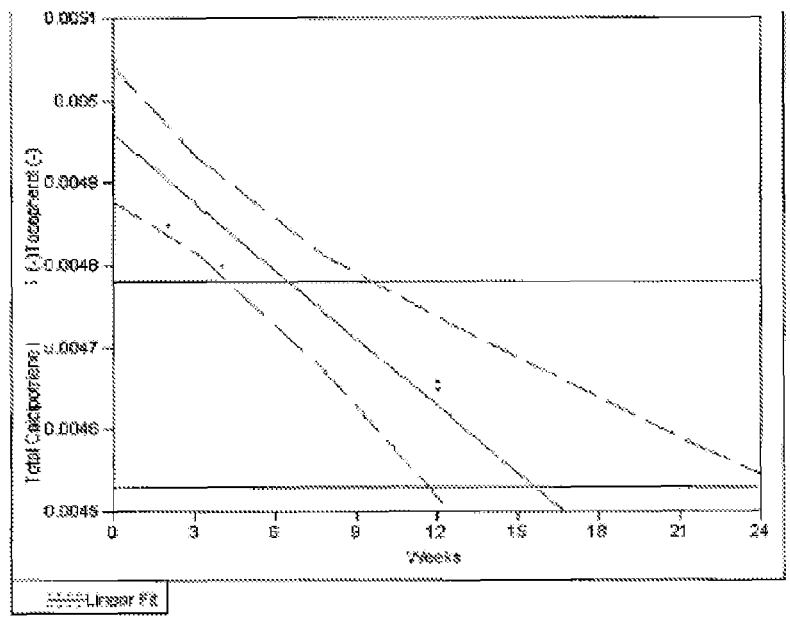
FIGS. 5 A-B show stability studies, Panel A shows the loss of calcipotriene without a stabilizer, Panel B shows enhanced stability of the active ingredient with the addition of a stabilizer.
Figure 5:
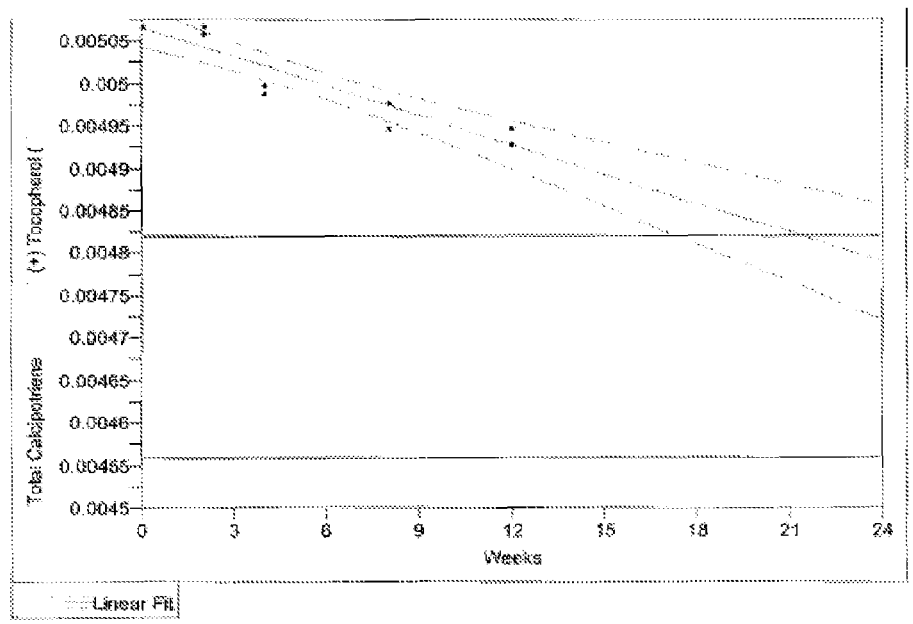
Figure 6:
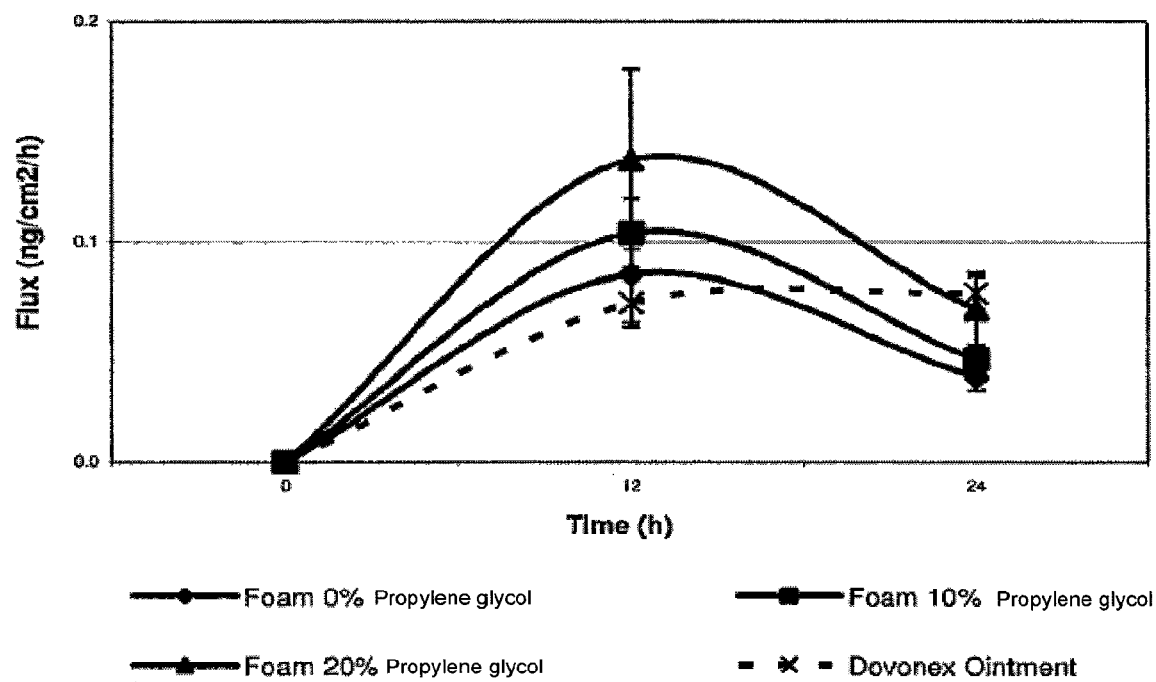
Figure 7:
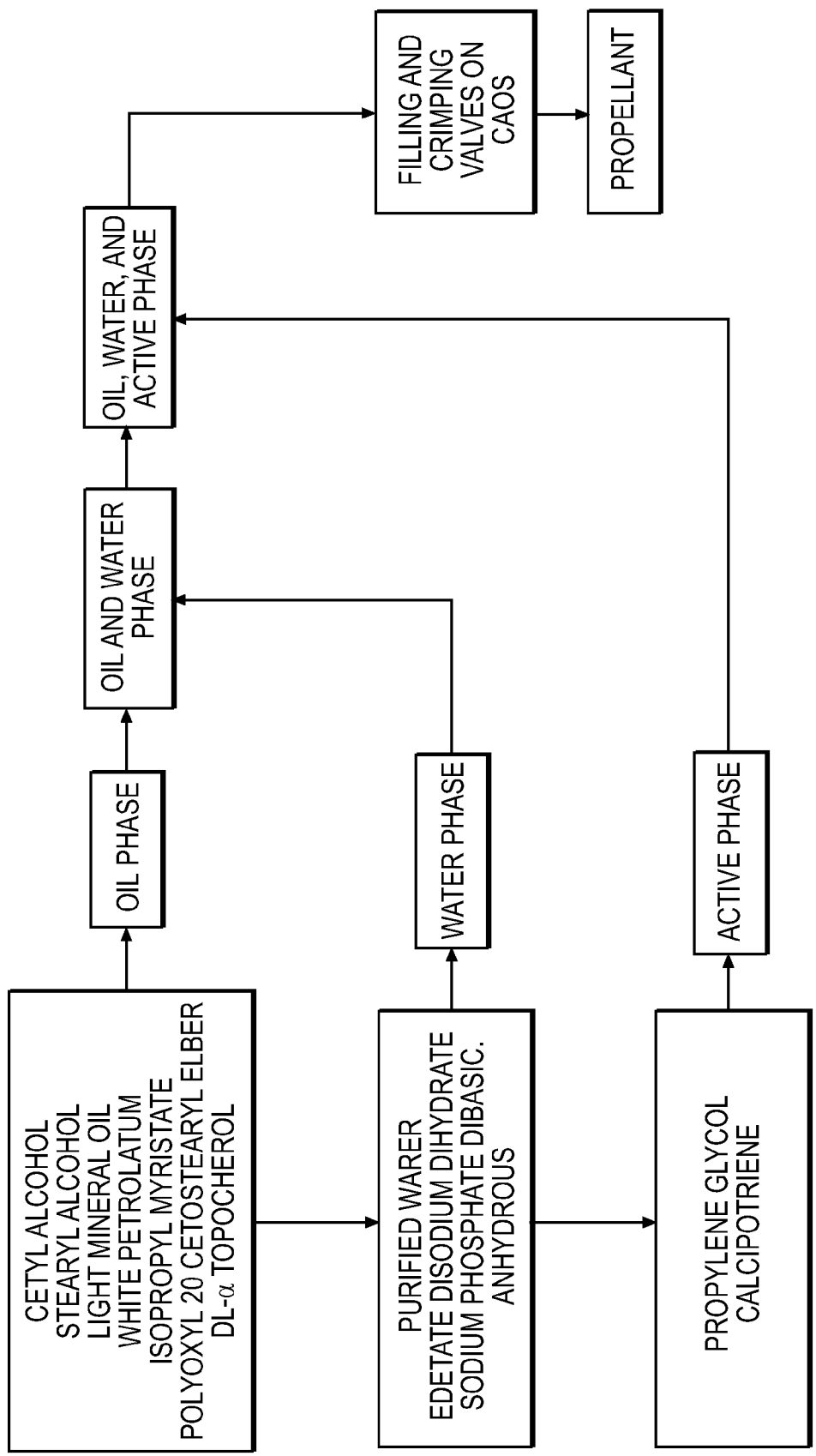
Figure 8A:
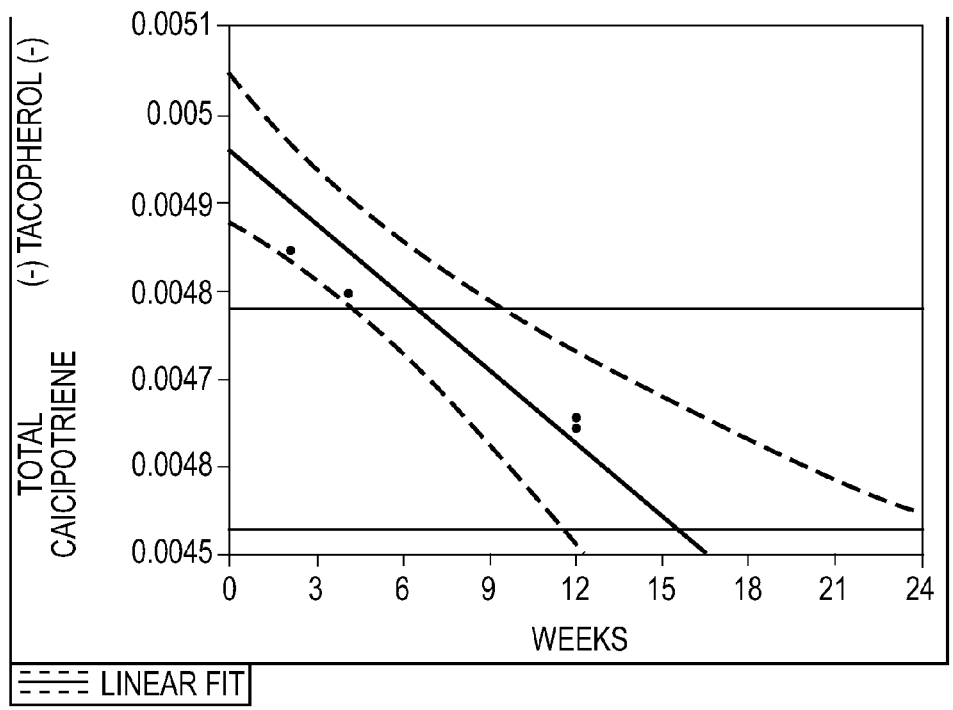
Figure 8B:
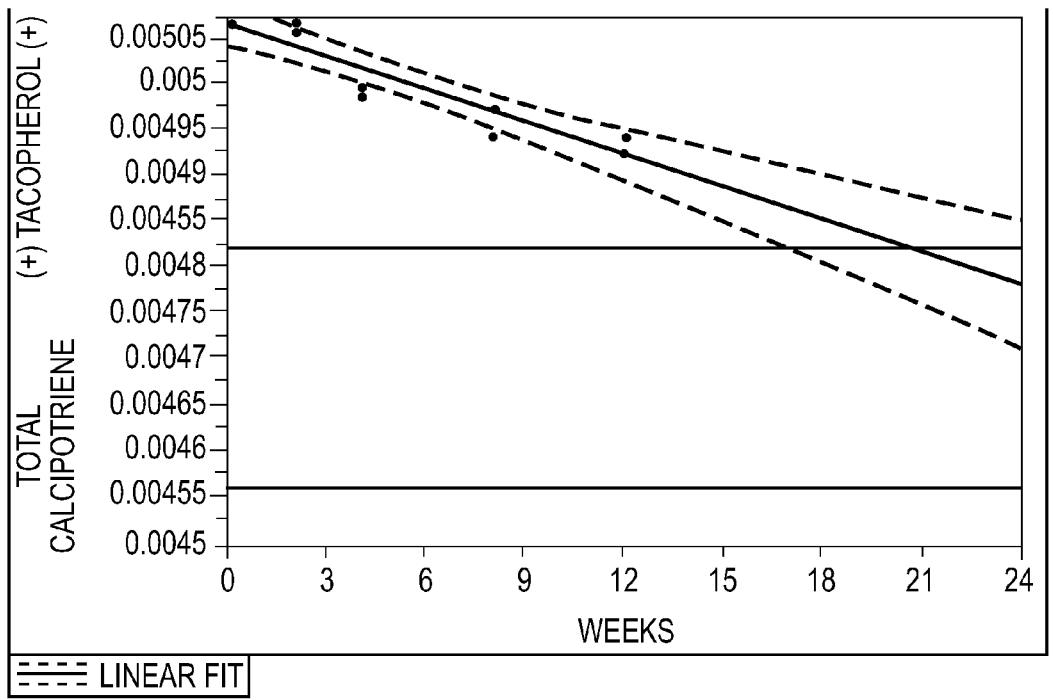

With reference to FIG. 5A, the results of a stability study are shown wherein a calcipotriene foam formulation without tocopherol degrades rapidly. The results are shown for a 12 weeks study at 40° C. However, as shown in FIG. 5B, the addition of alpha-tocopherol to the formulation enhances stability unexpectedly. The results are shown for a 12 weeks study at 40° C.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A topical oil-in-water emulsion composition, said topical oil-in-water emulsion composition comprising:
   a water phase and an oil phase;
   calcipotriene, wherein the calcipotriene is solubilized in said water phase and a stabilizer is solubilized in said oil phase;
   an emulsifier;
   an occlusive agent;
   an organic co-solvent;
   an aerosol propellant; and
   wherein said emulsion is an aerosol emulsion, which is a foam when released from a pressurized container, and the stabilizer prevents oxidation of the calcipotriene.

2. The topical oil-in-water emulsion composition of claim 1, wherein said calcipotriene is first solubilized in said organic co-solvent, which is water soluble.

3. The topical oil-in-water emulsion composition of claim 2, wherein said organic co-solvent is selected from the group consisting of propylene glycol, ethylene glycol, butylene glycol, a polyol, and mixtures thereof.

4. The topical oil-in-water emulsion composition of claim 1, wherein said stabilizer is selected from the group consisting of vitamin E, vitamin E derivatives, beta-carotene, coenzyme Q10, lutein, tocotrienols, soy isoflavones, s-adenosylmethionine, butylated hydroxytoluene, and a mixture thereof.

5. The topical oil-in-water emulsion composition of claim 4, wherein said stabilizer is vitamin E or a derivative thereof.

6. The topical oil-in-water emulsion composition of claim 1, wherein said calcipotriene is present in an amount of from about 0.0001% by weight to about 10% by weight, based on the total weight of the composition.

7. The topical oil-in-water emulsion composition of claim 1, wherein said composition comprises water in an amount up to 90% w/w, based on the total weight of the composition.

8. The topical oil-in-water emulsion composition of claim 7, wherein said composition comprises water in an amount from about 70% to about 90% w/w, based on the total weight of the composition.

9. The topical oil-in-water emulsion composition of claim 1, wherein said emulsifier is selected from one or more of the group consisting of a non-ionic, cationic or anionic surfactant, a fatty alcohol, a fatty acid, and fatty acid salts thereof.

10. The topical oil-in-water emulsion composition of claim 9, wherein said emulsifier is a mixture of a $C_{14}$-$C_{22}$ alcohol and a polyoxyethylene fatty alcohol ether.

11. The topical oil-in-water emulsion composition of claim 10, wherein said $C_{14}$-$C_{22}$ alcohol is selected from the group consisting of cetyl alcohol, stearyl alcohol, and a mixture thereof.

12. The topical oil-in-water emulsion composition of claim 3, wherein said organic co-solvent is propylene glycol.

13. The topical oil-in-water emulsion composition of claim 1, wherein said emulsifier is present in an amount of from about 2% to about 5% by weight, based on the total weight of the composition.

14. The topical oil-in-water emulsion composition of claim 9, wherein said emulsifier is a non-ionic surfactant selected from the group consisting of glycerol fatty acid esters, glycol fatty acid esters, polyhydric alcohol fatty acid esters, polyoxyethylene fatty acid esters, polyoxyethylene fatty alcohol ethers, polyoxyethylene sorbitan fatty acid esters, sorbitan esters, alkyl glycosides, fatty acid ethanolamides, and a mixture thereof.

15. The topical oil-in-water emulsion composition of claim 1, wherein said occlusive agent is selected from the group consisting of a mineral oil, grease, petrolatum, a fatty acid, an animal fat, a vegetable fat, a water insoluble polymer, and mixtures thereof.

16. The topical oil-in-water emulsion composition of claim 1, wherein said occlusive agent is present in an amount of about 1% to about 55% by weight, based on the total weight of the composition.

17. The topical oil-in-water emulsion composition of claim 16, wherein the occlusive agent is present in an amount of about 1% to about 10% by weight, based on the total weight of the composition.

18. The topical oil-in-water emulsion composition of claim 1, further comprising a buffering agent, and wherein the pH of said composition is from about 4 to about 9.

19. The topical oil-in-water emulsion composition of claim 9, wherein said emulsifier is a mixture of surfactants which are sorbitan monostearate and polysorbate 60.

20. The topical oil-in-water emulsion composition of claim 1, further comprising a viscosity modifying agent.

21. The topical oil-in-water emulsion composition of claim 20, wherein the viscosity modifying agent is isopropyl myristate.

22. The topical oil-in-water emulsion composition of claim 1, wherein said aerosol propellant is selected from the group consisting of a hydrocarbon, a chlorofluorocarbon, dimethyl ether, hydrofluorocarbons, and a mixture thereof.

23. The topical oil-in-water emulsion composition of claim 22, wherein said aerosol propellant comprises a mixture of hydrocarbons.

24. A method for treating a dermatological disorder in a human, said method comprising:
   administering a topical oil-in-water emulsion composition of claim 1, to treat said dermatological disorder.

25. The method of claim 24, wherein said dermatological disorder is psoriasis.

26. The topical oil-in-water emulsion composition of claim 1, wherein said emulsifier is a surfactant or blend of surfactants having an HLB value of about 9 to about 14.

27. The topical oil-in-water emulsion composition of claim 1, wherein said organic co-solvent is PEG 200, PEG 300, PEG 400, PEG 800, ethylene glycol monoethyl ether, diethylene glycol monoethyl ether, ethyl acetate, propylene carbonate, or n-methylpyrrolidone.

28. The topical oil-in-water emulsion composition of claim 1, wherein the composition further comprises a corticosteroid.

29. A topical oil-in-water emulsion composition, said topical oil-in-water emulsion composition comprising:
   a water phase comprising water and calcipotriene, which is solubilized in said water phase;
   an oil phase comprising an occlusive agent and a stabilizer that is Vitamin E or a derivative thereof solubilized in said oil phase;
   an emulsifier;
   an organic co-solvent;
   an aerosol propellant; and
   wherein said emulsion is an aerosol emulsion, which is a foam when released from a pressurized container, and the stabilizer prevents oxidation of the calcipotriene.

30. The topical oil-in-water emulsion composition of claim 29, wherein said calcipotriene is first solubilized in said organic co-solvent, which is water soluble.

31. The topical oil-in-water emulsion composition of claim 30, wherein said organic co-solvent is selected from the group consisting of propylene glycol, ethylene glycol, butylene glycol, a polyol, and mixtures thereof.

32. The topical oil-in-water emulsion composition of claim 31, wherein said organic co-solvent is propylene glycol.

33. The topical oil-in-water emulsion composition of claim 29, wherein said organic co-solvent is PEG 200, PEG 300, PEG 400, PEG 800, ethylene glycol monoethyl ether, diethylene glycol monoethyl ether, ethyl acetate, propylene carbonate, or n-methylpyrrolidone.

34. The topical oil-in-water emulsion composition of claim 29, wherein said calcipotriene is present in an amount of from about 0.0001% by weight to about 10% by weight, based on the total weight of the composition.

35. The topical oil-in-water emulsion composition of claim 29, wherein said composition comprises water in an amount up to 90% w/w, based on the total weight of the composition.

36. The topical oil-in-water emulsion composition of claim 35, wherein said composition comprises water in an amount from about 70% to about 90% w/w, based on the total weight of the composition.

37. The topical oil-in-water emulsion composition of claim 29, wherein said emulsifier is a surfactant or blend of surfactants having an HLB value of about 9 to about 14.

38. The topical oil-in-water emulsion composition of claim 29, wherein said emulsifier is selected from one or more of the group consisting of a non-ionic, cationic or anionic surfactant, a fatty alcohol, a fatty acid, and fatty acid salts thereof.

39. The topical oil-in-water emulsion composition of claim 38, wherein said emulsifier is a mixture of a $C_{14}$-$C_{22}$ alcohol and a polyoxyethylene fatty alcohol ether.

40. The topical oil-in-water emulsion composition of claim 39, wherein said $C_{14}$-$C_{22}$ alcohol is selected from the group consisting of cetyl alcohol, stearyl alcohol, and a mixture thereof.

41. The topical oil-in-water emulsion composition of claim 38, wherein said emulsifier is a non-ionic surfactant selected from the group consisting of glycerol fatty acid esters, glycol fatty acid esters, polyhydric alcohol fatty acid esters, polyoxyethylene fatty acid esters, polyoxyethylene fatty alcohol ethers, polyoxyethylene sorbitan fatty acid esters, sorbitan esters, alkyl glycosides, fatty acid ethanolamides, and a mixture thereof.

42. The topical oil-in-water emulsion composition of claim 38, wherein said emulsifier is a mixture of surfactants which are sorbitan monostearate and polysorbate 60.

43. The topical oil-in-water emulsion composition of claim 29, wherein said emulsifier is present in an amount of from about 2% to about 5% by weight, based on the total weight of the composition.

44. The topical oil-in-water emulsion composition of claim 29, wherein said occlusive agent is selected from the group consisting of a mineral oil, grease, petrolatum, a fatty acid, an animal fat, a vegetable fat, a water insoluble polymer, and mixtures thereof.

45. The topical oil-in-water emulsion composition of claim 29, wherein said occlusive agent is present in an amount of about 1% to about 55% by weight, based on the total weight of the composition.

46. The topical oil-in-water emulsion composition of claim 45, wherein the occlusive agent is present in an amount of about 1% to about 10% by weight, based on the total weight of the composition.

47. The topical oil-in-water emulsion composition of claim 29, further comprising a buffering agent, and wherein the pH of said composition is from about 4 to about 9.

48. The topical oil-in-water emulsion composition of claim 29, further comprising a viscosity modifying agent.

49. The topical oil-in-water emulsion composition of claim 48, wherein the viscosity modifying agent is isopropyl myristate.

50. The topical oil-in-water emulsion composition of claim 29, wherein said aerosol propellant is selected from the group consisting of a hydrocarbon, a chlorofluorocarbon, dimethyl ether, hydrofluorocarbons, and a mixture thereof.

51. A method for treating psoriasis in a human, said method comprising:
administering a topical oil-in-water emulsion composition of claim 29, to treat said psoriasis.

52. A topical oil-in-water emulsion composition, said topical oil-in-water emulsion composition comprising:
a water phase comprising water, a water soluble organic co-solvent, and calcipotriene present in an amount of from about 0.0001% by weight to about 10% by weight, based on the total weight of the composition, and which is first solubilized in said water soluble organic co-solvent and is further solubilized into said water phase;
an oil phase comprising an occlusive agent present in an amount of about 1% to about 10% by weight, based on the total weight of the composition, and a stabilizer that is Vitamin E or a derivative thereof solubilized in said oil phase;
an emulsifier present in an amount of from about 2% to about 5% by weight, based on the total weight of the composition;
an aerosol propellant; and
wherein said emulsion is an aerosol emulsion, which is a foam when released from a pressurized container, and the stabilizer prevents oxidation of the calcipotriene.

53. The topical oil-in-water emulsion composition of claim 52, wherein said water soluble organic co-solvent is selected from the group consisting of propylene glycol, ethylene glycol, butylene glycol, a polyol, and mixtures thereof.

54. The topical oil-in-water emulsion composition of claim 53, wherein said water soluble organic co-solvent is propylene glycol.

55. The topical oil-in-water emulsion composition of claim 52, wherein said water soluble organic co-solvent is PEG 200, PEG 300, PEG 400, PEG 800, ethylene glycol monoethyl ether, diethylene glycol monoethyl ether, ethyl acetate, propylene carbonate, or n-methylpyrrolidone.

56. The topical oil-in-water emulsion composition of claim 52, wherein said composition comprises water in an amount up to 90% w/w, based on the total weight of the composition.

57. The topical oil-in-water emulsion composition of claim 56, wherein said composition comprises water in an amount from about 70% to about 90% w/w, based on the total weight of the composition.

58. The topical oil-in-water emulsion composition of claim 52, wherein said emulsifier is a surfactant or blend of surfactants having an HLB value of about 9 to about 14.

59. The topical oil-in-water emulsion composition of claim 52, wherein said emulsifier is selected from one or more of the group consisting of a non-ionic, cationic or anionic surfactant, a fatty alcohol, a fatty acid, and fatty acid salts thereof.

60. The topical oil-in-water emulsion composition of claim 59, wherein said emulsifier is a mixture of a $C_{14}$-$C_{22}$ alcohol and a polyoxyethylene fatty alcohol ether.

61. The topical oil-in-water emulsion composition of claim 60, wherein said $C_{14}$-$C_{22}$ alcohol is selected from the group consisting of cetyl alcohol, stearyl alcohol, and a mixture thereof.

62. The topical oil-in-water emulsion composition of claim 59, wherein said emulsifier is a non-ionic surfactant selected from the group consisting of glycerol fatty acid esters, glycol fatty acid esters, polyhydric alcohol fatty acid esters, polyoxyethylene fatty acid esters, polyoxyethylene fatty alcohol ethers, polyoxyethylene sorbitan fatty acid esters, sorbitan esters, alkyl glycosides, fatty acid ethanolamides, and a mixture thereof.

63. The topical oil-in-water emulsion composition of claim 59, wherein said emulsifier is a mixture of surfactants which are sorbitan monostearate and polysorbate 60.

64. The topical oil-in-water emulsion composition of claim 52, wherein said occlusive agent is selected from the group consisting of a mineral oil, grease, petrolatum, a fatty acid, an animal fat, a vegetable fat, a water insoluble polymer, and mixtures thereof.

65. The topical oil-in-water emulsion composition of claim 52, further comprising a buffering agent, and wherein the pH of said composition is from about 4 to about 9.

66. The topical oil-in-water emulsion composition of claim 52, further comprising a viscosity modifying agent.

67. The topical oil-in-water emulsion composition of claim 66, wherein said viscosity modifying agent is isopropyl myristate.

68. The topical oil-in-water emulsion composition of claim 52, wherein said aerosol propellant is selected from the group consisting of a hydrocarbon, a chlorofluorocarbon, dimethyl ether, hydrofluorocarbons, and a mixture thereof.

69. The topical oil-in-water emulsion composition of claim 52, wherein the composition further comprises a corticosteroid.

70. A method for treating psoriasis in a human, said method comprising:
    administering a topical oil-in-water emulsion composition of claim 52, to treat said psoriasis.

* * * * *